US010406210B2

(12) United States Patent
Ding et al.

(10) Patent No.: US 10,406,210 B2
(45) **Date of Patent: *Sep. 10, 2019**

(54) HIGH-PURITY INHALABLE PARTICLES OF INSULIN AND INSULIN ANALOGUES, AND HIGH-EFFICIENCY METHODS OF MANUFACTURING THE SAME

(71) Applicant: Amphastar Pharmaceuticals Inc., Rancho Cucamonga, CA (US)

(72) Inventors: Jeffrey Ding, Rancho Cucamonga, CA (US); Aili Bo, Rancho Cucamonga, CA (US); Mary Ziping Luo, Rancho Cucamonga, CA (US); Jack Yongfeng Zhang, Rancho Cucamonga, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/280,508

(22) Filed: Sep. 29, 2016

(65) Prior Publication Data

US 2017/0196942 A1 Jul. 13, 2017

Related U.S. Application Data

(62) Division of application No. 14/990,787, filed on Jan. 7, 2016.

(51) Int. Cl.

| | |
|---|---|
| ***A61K 9/16*** | (2006.01) |
| ***A61K 9/00*** | (2006.01) |
| ***A61K 38/28*** | (2006.01) |
| ***A61K 9/14*** | (2006.01) |
| ***C07K 14/62*** | (2006.01) |

(52) U.S. Cl.

CPC .............. *A61K 38/28* (2013.01); *A61K 9/008* (2013.01); *A61K 9/0073* (2013.01); *A61K 9/143* (2013.01); *C07K 14/62* (2013.01)

(58) Field of Classification Search

CPC ........ A61K 38/28; A61K 33/30; A61K 38/00; A61K 9/0073; A61K 31/315; C07K 14/62

See application file for complete search history.

(56) References Cited

U.S. PATENT DOCUMENTS

| | | | |
|---|---|---|---|
| 5,952,297 | A | 9/1999 | De Felippis et al. |
| 5,985,309 | A | 11/1999 | Edwards et al. |
| 6,051,256 | A | 4/2000 | Platz et al. |
| 6,090,925 | A | 7/2000 | Woiszwillo et al. |
| 6,221,398 | B1 | 4/2001 | Jakupovic et al. |
| 6,310,038 | B1 | 10/2001 | Havelund |
| 6,444,226 | B1 | 9/2002 | Steiner et al. |
| 6,582,728 | B1 | 6/2003 | Platz et al. |
| 6,652,885 | B2 | 11/2003 | Steiner et al. |
| 7,087,246 | B2 | 8/2006 | Kim et al. |
| 7,374,782 | B2 | 5/2008 | Brown |
| 7,521,069 | B2 | 4/2009 | Patton et al. |
| 7,625,865 | B2 | 12/2009 | Colombo et al. |
| 7,648,960 | B2 | 1/2010 | Steiner et al. |
| 7,803,763 | B2 | 9/2010 | Thurow et al. |
| 7,943,178 | B2 | 5/2011 | Steiner et al. |
| 8,075,919 | B2 | 12/2011 | Brown et al. |
| 8,389,470 | B2 | 3/2013 | Steiner et al. |
| 2006/0292224 | A1 | 12/2006 | Moore et al. |
| 2008/0026068 | A1 | 1/2008 | Brown et al. |
| 2016/0008287 | A1 | 1/2016 | Ding et al. |

FOREIGN PATENT DOCUMENTS

| | | | |
|---|---|---|---|
| EP | 0709395 | A2 | 5/1996 |
| EP | 0735048 | A1 | 10/1996 |
| EP | 2 036 572 | A1 | 3/2009 |
| JP | 2007-531701 | | 11/2007 |
| WO | WO 98/42749 | A1 | 10/1998 |
| WO | WO 01/00674 | A1 | 1/2001 |
| WO | WO 2005/032511 | A2 | 4/2005 |
| WO | WO 2005/035088 | A2 | 4/2005 |
| WO | WO2013115965 | A1 | 8/2013 |
| WO | WO 2016/007682 | A1 | 1/2016 |

OTHER PUBLICATIONS

Jiang et al. (FEBS Letters, 2005, 579, 3927-3931). (Year: 2005).*

Lauryl Alcohol MSDS, Jeen International Corp., Material Safety Data Sheet, Jan. 4, 2004. (Year: 2004).*

Ask the TA: Chemistry Help, "Buffers," www.askthetachemistry-help.com/buffers.html, 2008, 2 pages.

Mark M. Bailey, et al., "Pure Insulin Nanoparticle Agglomerates for Pulmonary Delivery," National Institute of Health, Langmuir: Author Manuscript, Dec. 2, 2009, pp. 1-21.

Michael Somogyi, et al., "On the Preparation of Insulin," J. Biol. Chem. 1924, 60:31-58.

International Search Report dated Sep. 8, 2015 of the corresponding International Patent Application No. PCT/US2015/039625, noting listed references in this IDS (11 pages).

Black, C., et al., "The clinical effectiveness and cost-effectiveness of inhaled insulin in diabetes mellitus: a systematic review and economic evaluation," Health Technology Assessment, vol. 11, No. 33, Sep. 2007, pp. 1-126.

(Continued)

*Primary Examiner* — Kaipeen E Yang

(74) *Attorney, Agent, or Firm* — Lewis Roca Rothgerber Christie LLP

(57) ABSTRACT

A high-purity inhalable insulin material, used for preparing a pulmonary pharmaceutical product, includes insulin particles having a particle size at the micrometer level and having the following characteristics: (i) the purity of insulin is not less than 96% on the dried basis; (ii) the total amount of insulin-related impurities is not more than 2%; (iii) the total amount of solvent impurities, which is not a co-solvent formulation component for a pulmonary product, is not more than 0.03%; and (iv) the total amount of non-solvent impurities is not more than 0.3%. Up to 99% by volume of the insulin particles in the inhalable insulin have a particle size of less than 5 μm, based on the total volume of the insulin particles. A high-efficiency method prepares high-purity inhalable insulin material. The yield rate for the high-efficiency method is 75 to 85% or more.

24 Claims, 17 Drawing Sheets

(56) References Cited

OTHER PUBLICATIONS

Butterfield, Timothy A., et al., "The Dual Roles of Neutrophils and Macrophages in Inflammation: A Critical Balance Between Tissue Damage and Repair," Journal of Athletic Training, vol. 41, No. 4, 2006, pp. 457-465.
Chordiya, Gangurde H.H., et al., "Approaches and Devices Used in Pulmonary Drug Delivery System: a Review," Asian Journal of Pharmaceutical Research & Health Care, vol. 4, No. 1, 2012, pp. 11-27.
Chow, Albert H. L., et al., "Particle Engineering for Pulmonary Drug Delivery," Pharmaceutical Research, vol. 24, No. 3, Mar. 2007, pp. 411-437.
Ehmer, Alex, "Micronization of Proteins by Jet Milling," Dissertation, Universität Regensburg, 2009, Chapter 1, p. 8.
"FDA Approves First Ever Inhaled Insulin Combination Product for Treatment of Diabetes," News & Events, Jan. 27, 2006 (3 pages).
Heyder, Joachim, "Deposition of Inhaled Particles in the Human Respiratory Tract and Consequences for Regional Targeting in Respiratory Drug Delivery," Proceedings of the American Thoracic Society, vol. 1, 2004, pp. 315-320.
Pikal, M. J., et al., "Formulation and Stability of Freeze-Dried Proteins: Effects of Moisture and Oxygen on the Stability of Freeze-Dried Formulations of Human Growth Hormone," International Symposium on Biological Product Freeze-Drying and Formulation, vol. 74, 1990, pp. 21-38.
Ragab, Doaa M., et al., "Particle Engineering Strategies via Crystallization for Pulmonary Drug Delivery," Organic Process Research & Development, vol. 13, No. 6, 2009, pp. 1215-1223.
Skyler, Jay, "Pulmonary insulin: current status," Diabetes Voice, vol. 51, Issue 1, Mar. 2006, pp. 23-25.
Whittingham, Jean L., et al., "Insulin at pH 2: Structural Analysis of the Conditions Promoting Insulin Fibre Formation," J. Mol. Biol., vol. 318, No. 2, 2002, pp. 479-490.
Sigma, Product Information for Insulin from bovine pancreas, Catalog No. I5500, 2014, 2 pages.
Sigma Product Information, Insulin, Human, Recombinant Expressed in *E. coli*, Product Nos. I0259 and I2767, 1999, 2 pages.
Biological Buffers, AppliChem, 2008, 20 pages.
Lando, Howard M., The New "Designer" Insulins, Clinical Diabetes, vol. 18, No. 4, Fall 2000, pp. 1-12.
Vandana, et al., An overview on in situ micronization technique—An emerging novel concept in advanced drug delivery, Saudi Pharmaceutical Journal, 2014, pp. 283-289.
PCT International Search Report and Written Opinion dated Jun. 22, 2016 for International Application No. PCT/US2016/012715, 13 pages.
Gupte, Suraj, "Noninvasive Delivery of Insulin Pulmonary Delivery," p. 325 of *Recent Advances in Pediatrics—17: Hot Topics*, First Edition 2007 ISBN 81-8448-103-9, 3 pages.
Office action issued in U.S. Appl. No. 14/794,766, dated Feb. 18, 2016, 14 pages.
Office action issued in U.S. Appl. No. 14/794,766, dated Nov. 4, 2016, 19 pages.
Office action issued in U.S. Appl. No. 14/794,766, dated Jul. 5, 2017, 21 pages.
Office action issued in Japanese Application No. 2017-500986, dated Oct. 31, 2017, 8 pages.
Hallas-Moller, K., et al., Crystalline and Amorphous Insulin-Zinc Compounds with Prolonged Action, Science, vol. 116, Oct. 10, 1952, 5 pages.
Russian Office action issued in Application No. 2017103751, dated Apr. 5, 2018, 18 pages.
U.S. Office action issued in U.S. Appl. No. 14/990,787, dated Apr. 24, 2018, 11 pages.
Office Action issued in Canadian Patent Application No. 2,954,287, dated Feb. 13, 2018, 4 pages.
Office action issued in Japanese Patent Application No. 2017-500986, dated Oct. 2, 2018, 12 pages.
Koichi Katoh, "Acidity in water-alcohol mixtures," Bunseki Kagaku, vol. 15, Issue 8, 1966, pp. 811-816.

* cited by examiner

HIGH-PURITY INHALABLE PARTICLES OF INSULIN AND INSULIN ANALOGUES, AND HIGH-EFFICIENCY METHODS OF MANUFACTURING THE SAME

CROSS REFERENCE TO RELATED APPLICATIONS

This application is a divisional of U.S. patent application Ser. No. 14/990,787 filed Jan. 7, 2016 the contents of which is hereby incorporated by reference in its entirety.

FIELD

Embodiments of the invention relate in general to pulmonary delivery of high-purity human insulin and/or a human insulin analogue, and a high-efficiency process for manufacturing particles of insulin (e.g., human insulin and/or a human insulin analogue) for pulmonary delivery. Aspects of embodiments of the disclosure also relate in general to compositions including insulin particles (e.g., human insulin particles and/or human insulin analogue particles) having improved particle characteristics.

BACKGROUND

Growing attention has been given to the potential of a pulmonary delivery route for non-invasive administration and systemic delivery of therapeutic agents (mainly peptides and proteins) because the lungs are capable of providing a large absorptive surface area (up to 100 $m^2$) and have absorptive mucosal membranes that are very or extremely thin (e.g., have a thickness of about 0.1 μm-0.2 μm) and have good blood supply. A very thin alveolar-capillary and a bronchial-capillary barrier on a surface of the lungs allows for rapid uptake of human insulin particles into a subject's bloodstream, at a rate similar to that achieved with the rapid-acting human insulin analogue, which is an altered form of human insulin that is different from human insulin that occurs in nature, but still functions in the human body in a manner similar to human insulin, but with better performance in terms of glycemic control.

Insulin formulations may be administered by subcutaneous or intravenous injection. Inhaled insulin appears to be as effective as injected short-acting insulin. Pulmonary delivery technology was developed so that inhaled insulin can effectively reach the lung capillaries where it is absorbed.

Human lung airways contain bronchial tubes, which are impermeable to insulin, as well as alveoli. Inhaled insulin can be absorbed through the alveoli and enter into the circulation system. Inhaled asthma medications deposit before reaching the alveoli. Devices can deliver human insulin particles via slow and even breaths into the alveoli, and the human insulin can be released into the circulation system.

Inhaled human insulin may be used for pre-meal insulin delivery in people with type I and/or II diabetes. Its use may also facilitate the early introduction of insulin therapy to people who are averse to insulin injections due to reactions, such as inflammation, bruising, anxiety, and the like.

SUMMARY

According to an embodiment of the present disclosure, a method of preparing an inhalable insulin (e.g., human insulin, animal insulin, and/or a human insulin analogue) suitable for pulmonary delivery includes: dissolving an insulin raw material in an acidic solution (e.g., a mixture of water and methanol) to form a dissolved insulin solution; titrating the dissolved insulin solution with a buffer solution to form a suspension comprising insulin particles; stabilizing the insulin particles with ethanol; concentrating; and washing with ethanol and concentrating to obtain insulin particles with a particle size at the micrometer level suitable for pulmonary pharmaceutical drugs.

The acidic solution may include water, an organic solvent, e.g. methanol, or a mixture thereof.

The acidic solution may include the organic solvent in an amount of 10 to 90 vol %, based on the total volume of the acidic solution.

The acidic solution may include the organic solvent in an amount of greater than 0 to 90 vol % of the total volume of the acidic solution.

The organic solvent may include an alcohol.

The alcohol may include methanol, ethanol, or a mixture thereof.

The buffer solution may have a pH of 3 to 10.

The stabilizing of the micronized insulin particles may include adding a stabilizing agent to the suspension.

The stabilizing agent may have a neutral pH and may be miscible with water.

The stabilizing agent may include an alcohol, a ketone, or a mixture thereof.

The stabilizing may increase the yield of the micronized insulin particles.

The micronized insulin particles may be prepared at a pH of 3 to 9.

The micronized insulin particles may be prepared at a pH of 4.5 to 7.5.

The micronized insulin particles may include substantially spherical particles having a volume mean diameter of about 1 to 2 μm (e.g., 1.2 to 2 μm).

The micronized insulin particles may include up to 99 vol % of particles having a particle size of less than 5 μm, based on the total volume of the micronized insulin particles.

The acidic solution may have a pH range of 1.0 to 3.0. For example, the acidic solution may have a pH in a range of 1.5 to 2.5 (e.g., 1.5 to 2.5).

The acidic solution may have a pH of about 2 and may include water and 10 vol % to 90 vol % of an organic solvent including methanol, ethanol, or a mixture thereof, based on the total volume of the acidic solution.

The micronized insulin particles may be substantially spherical in shape and may have a particle size of less than 5 μm.

The micronized insulin particles may include an insulin including human insulin, an animal insulin, an insulin analogue, or a mixture thereof.

The insulin analogue may include insulin aspart, insulin glargine, or a mixture thereof.

The dissolving, the titrating, and/or the stabilizing procedures may be performed at room temperature.

The insulin raw material may include a crystalline insulin including crystalline human insulin, a crystalline animal insulin, a crystalline insulin analogue, or a mixture thereof.

The crystalline insulin analogue may include crystalline insulin aspart, crystalline insulin glargine, or a mixture thereof.

According to an embodiment of the present disclosure, micronized insulin particles include substantially spherical particles comprising an insulin selected from the group consisting of human insulin, an animal insulin, an insulin analogue, and a mixture thereof.

The obtained inhalable insulin particles have high purity of insulin (e.g., >98% on the dried basis, e.g., >98% by weight based on the total weight of the insulin particles on a dried basis) and low impurities, such as, for example: insulin-related impurities are less than 2% on the dried basis, e.g., less than 2% by weight based on the total weight of the insulin particles on a dried basis; total amount of solvent impurities are less than 0.03% on the dried basis, e.g., less than 0.03% by weight based on the total weight of the insulin particles on a dried basis, (where the solvent impurities do not include a co-solvent component for the pulmonary drug formulation), and non-solvent impurities are less than 0.3% on the dried basis, e.g., 0.03% by weight based on the total weight of the insulin particles on a dried basis.

The disclosed method has a high-efficiency. The yield generated for the insulin particles is in the range of 75-85% by weight, or even higher, based on the total weight of the final product. For example, the yield of insulin particles may be 75% or more by weight (e.g., 85% or more by weight) based on the total weight of the final product.

The substantially spherical particles may have a volume mean diameter of about 1.2 to 2 μm.

Up to 99 vol % of the substantially spherical particles may have a particle size of less than 5 μm, based on the total volume of the micronized insulin particles.

The insulin analogue may include insulin aspart, insulin glargine, or a mixture thereof.

The foregoing description of embodiments of the present disclosure is not meant to be an exhaustive summary, inasmuch as additional pertinent aspects of the present disclosure will be readily apparent to those skilled in the art from the following detailed description, taken independently or in conjunction with the accompanying drawings and tables, in which one or more embodiments of the invention are described and shown.

BRIEF DESCRIPTION OF THE DRAWINGS

The accompanying drawings, together with the specification, illustrate embodiments of the present disclosure, and, together with the description, serve to explain the principles of the present disclosure.

DETAILED DESCRIPTION

Figure 1:
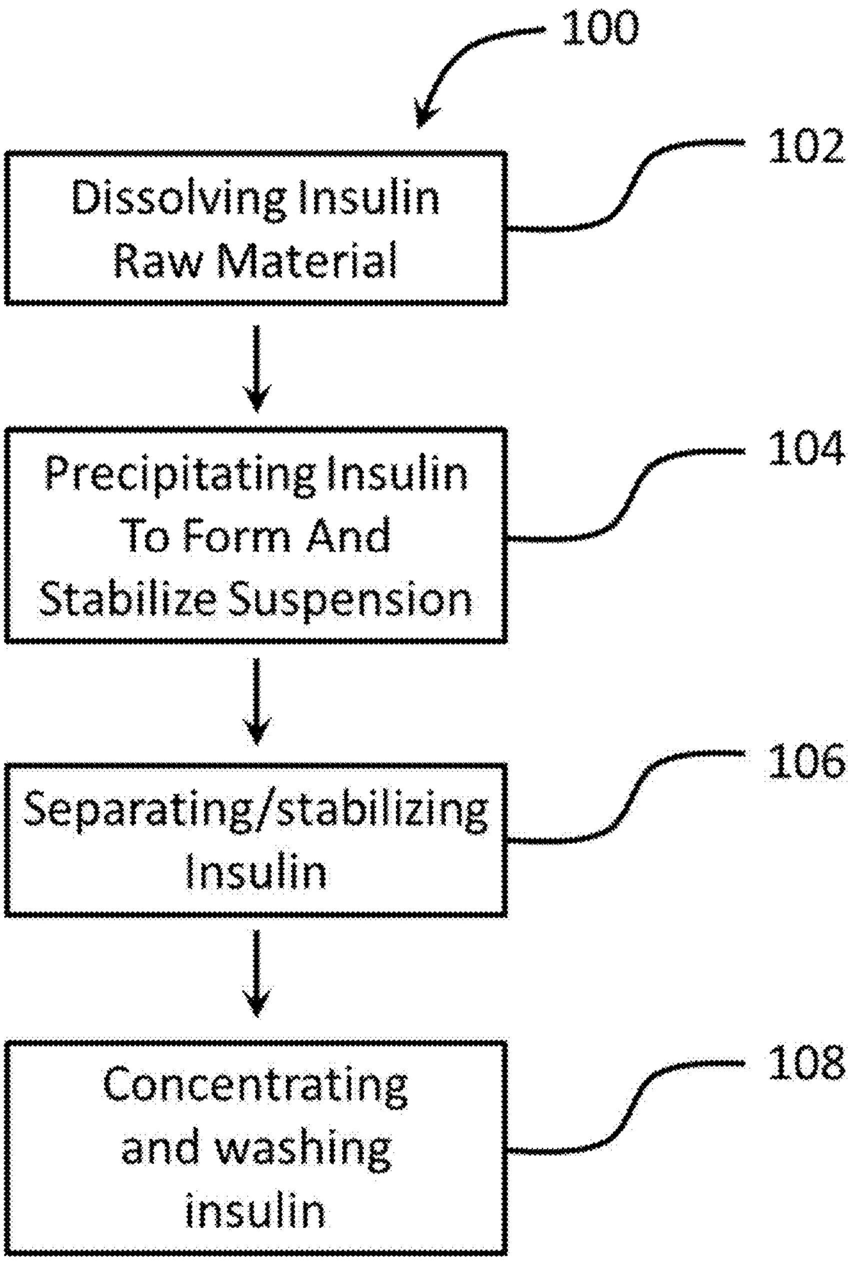
FIG. 1 is a flow chart illustrating an embodiment of a process for micronizing insulin and/or an insulin analogue.

The following detailed description is provided only for purposes of illustration of certain specific embodiments of the present disclosure and not for purposes of limiting the scope of the present invention. Alternate embodiments will be readily apparent to those skilled in the art and are intended to be included within the scope of the present invention. Also, in the context of the present application, the term "insulin" is used in a broad sense and encompasses any form of insulin or insulin analogue that can be used to treat a human or animal. For example, as used herein, the term "insulin" encompasses natural or synthetic human insulin, natural or synthetic animal insulin, and insulin analogues (e.g., insulin aspart, insulin glargine, and the like).

An embodiment of a micronization process for preparing inhalable insulin particles for pulmonary delivery includes: dissolving an insulin raw material (e.g., a crystalline insulin and/or a crystalline insulin analogue) in an acidic environment (e.g., dissolving in an acidic solution to facilitate dissolution of the insulin raw material) to form a dissolved insulin solution; titrating the dissolved insulin solution with a buffer solution to form a suspension including insulin particles having a particle size at the micrometer level; and adding a stabilizing agent (e.g., an organic solvent and/or a co-solvent) to stabilize the insulin particles (e.g., to increase the yield of the insulin particles before purification and drying) at 0 to 25° C.; concentrating the suspension; washing the suspension with a solvent (e.g., ethanol) at 0 to 25° C. then concentrating, where washing/concentrating may be conducted multiple times.

Embodiments of the process are conducted at room temperature or lower temperature and avoid or reduce the introduction of high temperatures (which will cause a reduction of the purity of insulin and also will result in an increase of impurities), avoid special chemical reagents (which will introduce more non-solvent impurities), avoid long duration processes (which will generate more insulin-related impurities even at room temperature), and avoid mechanical forces such as those introduced by jet milling processes. Some embodiments of the process are performed without addition of a polymer (e.g., an excipient polymer, such that a significant amount of polymer would exist in the obtained insulin particles) to the acidic environment, including the dissolved insulin solution and/or the suspension.

Embodiments of the present invention provide a process for the production of high-purity inhalable insulin that is suitable for pulmonary delivery. Embodiments of the process utilize raw crystalline insulin, which may have particle sizes in a sub-millimeter range, to provide inhalable insulin particles having a particle size in a micrometer range as an active pharmaceutical ingredient (API) for pulmonary delivery having improved characteristics, including more spherical shape, as well as improved smoothness. As described herein, the particle size or particle diameter (e.g., volume mean diameter) may be measured by a laser diffraction method, unless otherwise specified.

Pulmonary delivery of a drug particle is affected by the characteristics of the drug particle including particle size, particle shape, surface roughness, solubility, flowability, and/or the like. Since inhalable insulin and/or insulin analogues are an active drug ingredient and not just a passive carrier, embodiments of the present disclosure maintain or substantially maintain biological activities while micronizing the insulin and insulin analogues as high-purity insulin particles.

As reported above, the obtained insulin particles will be used to prepare pulmonary pharmaceutical drugs. Besides the particle size, the high-purity of insulin and low impurities will be important.

A particle having a particle size (or an aerodynamic diameter) of <5 μm allows for the inhaled drug to be absorbed by the lungs. Particles having a suitable aerodynamic diameter or particle size have good flow properties and are more easily dispersed into the lower airways (bronchial and alveolar regions) in which the absorption into the bloodstream is improved or optimized via alveolar-capillary surfaces of the lungs. On the other hand, over-sized drug particles (e.g., particles having an aerodynamic diameter or particle size >5 μm) would be mostly captured in the upper airways such as the throat and trachea by inertial impaction. The over-sized particles are substantially not absorbed as they accumulate in the upper airways, which do not have the thin penetrable capillaries of the alveoli. The accumulated drug particles may trigger the pulmonary defense system, which may prompt macrophages increment. The stimulation or excessive stimulation of macrophages may lead to recruitment of other inflammatory cells and may eventually produce secondary tissue damage, regeneration and fibrosis.

Drug particle size may play a determinant role in pulmonary delivery. To fabricate particles having a particle diameter <5 μm, a number of single-step micronization methods may be used, such as spray drying and mechanical milling technologies, such that after the process, the starting raw insulin powder particles, which in general have a diameter of millimeter range, have a diameter in a micrometer range for pulmonary delivery.

However, those processes for micronizing insulin particle involve introduction of heat at high temperature, lengthy processes, and/or excipient polymers and special chemical reagents during the insulin micronization process, which may cause aggregation and loss of activity of the insulin, reduce its purity, or introduce more impurities, and which may hinder pharmaceutical manufacturing. In addition, although the excipient polymer and other special reagents help to stabilize the formulation and increase the solubility during processing, the excipient polymer and other special reagents may introduce impurities that are difficult to remove.

It has also been found that micro-particles of insulin are formed by dissolving crystalline insulin at a pH near the isoelectric point of the insulin, when a polymer is used in the process of forming the insulin micro-particles. Various suitable types of polymers such as polyethylene glycol (PEG), polyvinylpyrrolidone (PVP), poly-lactic acid-co-glycolide acid (PLGA), as well as bioadhesive mechanisms, may be used in the process. When the polymer is added to the buffer solution, it may help to further increase the solubility of the crystalline insulin. However, the added polymer may not be efficiently and completely removed after the process. The residual polymer that is not removed may reduce drug efficacy, increase toxicity, and increase the level of impurities.

Other processes related to the production of microspheres that contain insulin introduce excipient polymers such as PVP, or PEG to help dissolve insulin in an acidic environment. Microspheres produced by such processes are exposed to relatively high temperatures that may be hazardous or damaging to insulin. At the end of such processes, an organic solvent (which has low solubility for insulin) for washing the polymer away may cause agglomeration of small insulin particles. Also, the foregoing organic solvents can denature insulin molecules contained in the microspheres and may also be toxic when administered to humans or animals.

Some insulin particles obtained by microencapsulation (e.g., by way of a surfactant) of uniform microcrystals of insulin using biodegradable polymeric materials. Such compositions, however, may have a low insulin content, for example, an average insulin particle may contain only 10 to 30% insulin w/w, based on the total weight of the insulin particle.

Aspects of embodiments of the present disclosure are directed toward overcoming the above-mentioned difficulties and generate high-purity insulin particles for pulmonary pharmaceutical products An embodiment of a method of manufacturing an inhalable insulin or insulin analogue may include the following four (4) actions:

(1) Dissolving an insulin raw material (e.g., crystalline insulin or insulin analogue) in an acidic environment to facilitate dissolution of the insulin raw material, thereby forming a dissolved true insulin solution. The acidic environment may include an acidic solution. For example, the acidic environment may include an acidic solution including water, an organic solvent (e.g., an alcohol, such as methanol), or a mixture thereof.

The behavior of insulin in an acidic environment may be utilized to dissolve insulin. In some embodiments, the acidic environment has a pH of about 1.0 to 3.0, for example, 1.5 to 2.5 (e.g., 1.8 to 2.5), to provide good dissolution conditions.

(2) Titrating the dissolved insulin solution with a buffer solution until the status of a suspension is reached (e.g., until a suspension is obtained). The titrating of the dissolved insulin solution causes the dissolved insulin to precipitate as insulin particles having a suitable particle size and shape and to form a suspension. As insulin precipitates the dissolved insulin solution changes from a clear or substantially clear solution to a milky and whitish suspension (e.g., the suspension including micronized insulin particles).

(3) Stabilizing the micronized insulin particles by adding a stabilizing agent (e.g., an organic solvent ethanol) to increase the yield of the insulin particles. The stabilizing agent may be added at room temperature or lower temperature in the range of 0-25° C. The stabilizing agent (e.g., the organic solvent and, optionally, the co-solvent) utilized may be varied according to the type of insulin and will be further described in the following section. Then, the suspension will be concentrated.

(4) the concentrated suspension of the insulin particles then will be washed with the same solvent (e.g., the same kind of solvent) at room temperature or lower temperature in the range of 0-25° C. This washing/concentrating may be conducted multiple times.

The above process will generate high-purity insulin particles. The obtained inhalable insulin particles have high purity of insulin (e.g., >98% on the dried basis, e.g., >98% by weight based on the total weight of the insulin particles on a dried basis) and low impurities, such as, for example: insulin-related impurity is less than 2% on the dried basis, e.g., less than 2% by weight based on the total weight of the insulin particles on a dried basis; the amount of total solvent impurities are less than 0.03% on the dried basis, e.g., less than 0.03% by weight based on the total weight of the dried insulin particles (where the solvent is not a co-solvent component for the pulmonary drug formulation), and the amount of non-solvent impurity is less than 0.3% on the dried basis, e.g., less than 0.3% by weight based on the total weight of the dried insulin particles on a dried basis. As used herein, unless otherwise indicated, the term "dried basis" indicates that the ingredient (or component, e.g., insulin particles or insulin) referenced need not be dried prior to use if due allowance is used with water or other volatile substances present in the quantity taken.

The disclosed method has a high-efficiency, the yield to generate the insulin particles having particle sizes at the micrometer level is in the range of 75-85% or even higher (e.g., 75% or more, or 85% or more based on the total weight of the final product).

Because of the high purity of insulin obtained, and low levels of other impurities, the obtained insulin particles can be used for further processing of pulmonary pharmaceutical products, such as (i) directly adding, or drying then adding, propellant (HFA 134a or 227) and other formulation components for a metered dose inhalation (MDI) product, or (ii) drying then mixing with a carrier (such as lactose) for a dry powder inhalation product.

Aspects of embodiments of the present disclosure provide the following features: high-purity inhalable insulin particles can be manufactured at high efficiency as compared to other processes.

Embodiments of the novel process for the inhalable particles of insulin and insulin analogues at room temperature for pulmonary delivery according to the present disclosure include the following four major steps. First, dissolution of an insulin raw material having a particle size in the sub-millimeter range in an acidic solvent as a true solution; second, generating insulin particles with a suitable particle size by titrating at suitable condition (pH, concentration, mixing, time etc.); third, stabilizing the generated insulin particles with a solvent (e.g., ethanol), then concentrating at 0-25° C.; and fourth, and, optionally, last, washing with solvent at 0-25° C. and concentrating.

In the first act, the insulin raw material may be dissolved in an acidic environment (e.g., an acidic solution) including water and an organic solvent that is polar, has a small molecular weight and is miscible with water. Methanol and/or ethanol may be used in the solution in an amount of up to 90 volume percent (vol %), based on the total volume of the solution, to control the starting solubility of insulin. For example, methanol and/or ethanol may be included in the acidic solution in an amount preferably of approximately 90 vol % (based on the total volume of the acidic solution), but any amount greater than 0 to up to 90 vol % is contemplated and may be used.

The acidic solution may be placed on top of a stirring plate. Steady, continuous, or substantially continuous stirring, such as 40 to 200 rotations per minute (rpm), may be utilized throughout until the solution becomes completely or substantially completely clear.

In the second act, the stirring speed may be slowed down, such as 30 to 100 rpm. The dissolved insulin solution is titrated or slowly titrated with a buffer solution, such as sodium acetate/acetic acid and precipitation of the insulin gradually appears as the dissolved insulin solution changes from a clear or substantially clear solution to a milky whitish suspension and gradually growing up to suitable particle size.

The particles of insulin and/or insulin analogue may be generated at a pH range of 3 to 9, for example, a pH range of 4.5 to 7.5. The buffer solution may be prepared to have same pH range.

In the third act, a stabilizing agent having a neutral pH and at temperature of 0-25° C. and that is miscible with water is utilized. Examples of the stabilizing agent include an alcohol and/or a ketone. For example, the alcohol may include ethanol, or a mixture thereof. The stabilizing agent stabilizes the micronized insulin particles. The stabilized suspension then will be concentrated.

In the fourth act, the concentrated suspension will be washed with solvent such as ethanol at 0-25° C. and further concentrated. The washing/concentrating may be repeated multiple times.

The obtained insulin particles can be used for further processing of pulmonary pharmaceutical products, such as (i) directly adding, or drying then adding, propellant (HFA 134a or 227) and other formulation components for a metered dose inhalation (MDI) product or (ii) drying then mixing with carrier (such as lactose) for a dry powder inhalation product.

FIG. 1 is a process flow chart illustrating an embodiment of a method for micronizing insulin and/or insulin analogues at room temperature. In FIG. 1, an embodiment of a process 100 for micronizing insulin includes dissolving insulin raw material 102, precipitating (e.g., by titrating) insulin to form and stabilize a suspension 104, separating/stabilizing insulin 106, and washing and concentrating insulin 108.

Embodiments of the present disclosure will now be described with reference to examples for purposes of illustration. The present disclosure, however, is not limited to the examples described herein.

EXAMPLE 1

Preparation of Inhalable Insulin Particles in a 90 Vol % Methanol Solution 70 mg of biosynthetic human insulin (i.e. from Amphastar France Pharmaceuticals, S.A.S.) raw material powder was dissolved in 7.7 ml of an acidic solution having a pH of about 1.9, which is a mixture of 90 vol % of methanol 10 vol % water, in a 40 ml vial. The vial was placed on top of a stirring plate and the resultant solution was steadily stirred until the solution was completely dissolved or substantially clear to form insulin true solution. Then, the stirring was slowed to a slower mode (e.g., a spinning speed of about 75 rpm), and 1.75 ml of a 0.1 M sodium acetate/Acetic Acid (NaAc/HAc) buffer solution having a pH of 5.64 (1.825 g NaAc and 0.165 g Acetic Acid dissolved into 250 ml solution) was added dropwise to slowly titrate the dissolved insulin solution. The clear dissolved insulin solution turned into a milky and yellowish suspension including micronized insulin particles. About 10 ml of ethanol (no PH adjusted ethanol) was added to the suspension after the titration was completed or substantially completed. The stirring was continued for another 30 minutes for stabilizing the particles and higher yield. The micronized insulin particles were separated from a supernatant of the suspension as a solid by centrifuge and the obtained solid was washed with ethanol twice to remove methanol and salt. The solid was vacuum dried at room temperature.

Figure 2:
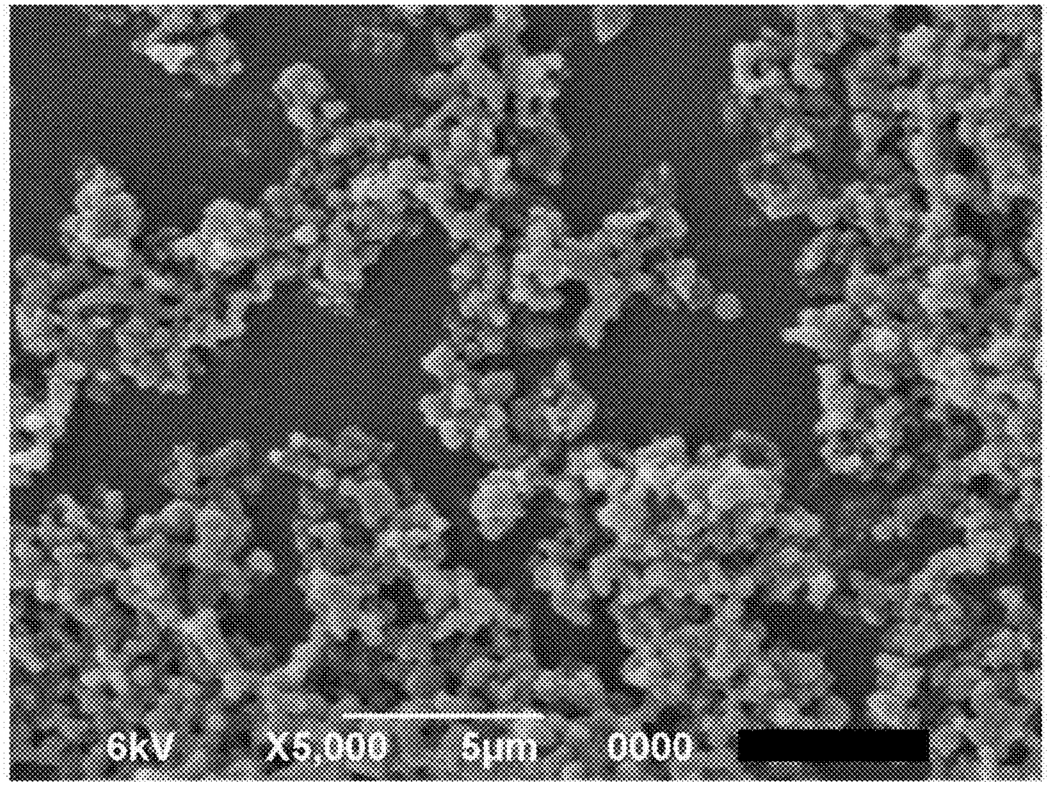
FIG. 2 is a Scanning Electron Microscopy (SEM) Image of micronized human insulin particles prepared according to an embodiment of the present disclosure.
Figure 3:
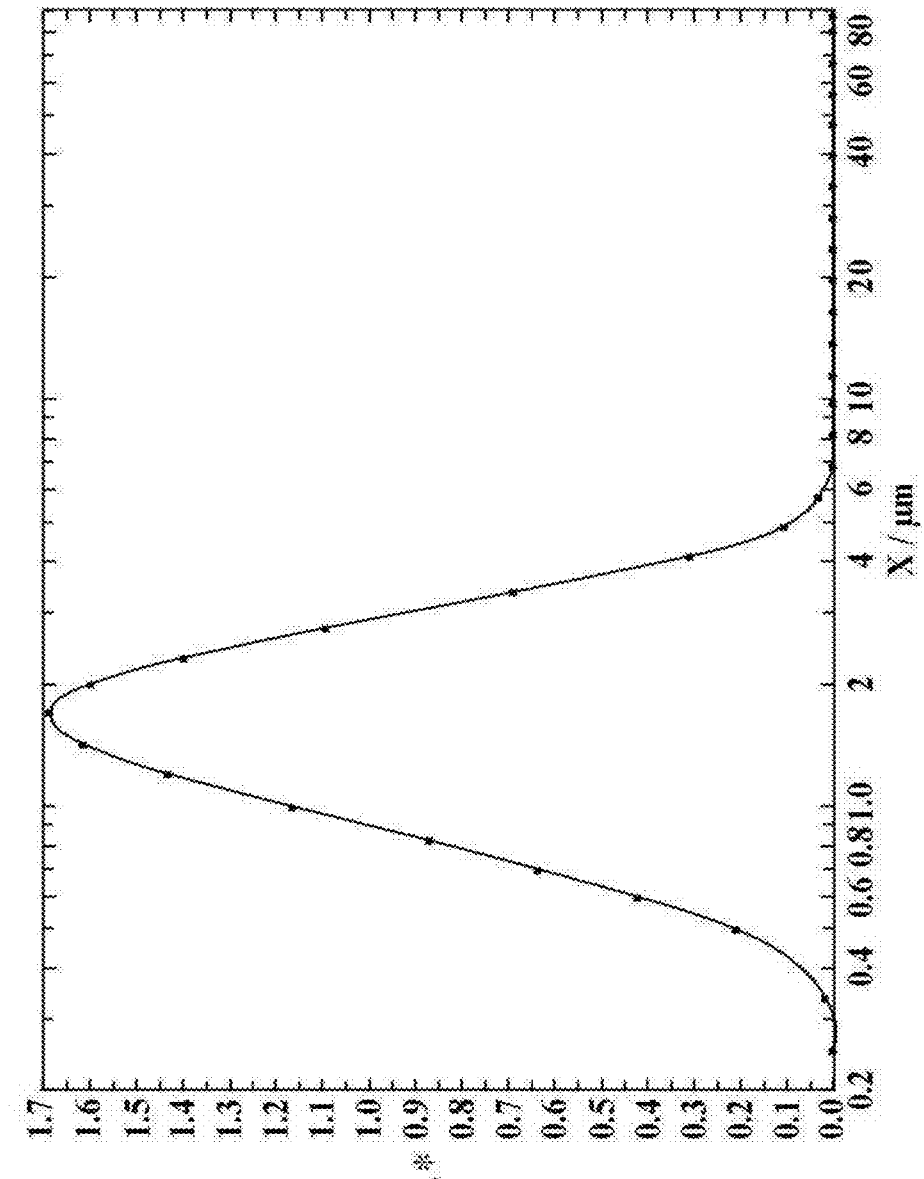
FIG. 3 is a graph illustrating a particle size distribution of micronized human insulin particles prepared according to the embodiment of FIG. 2.

FIG. 2 is a scanning electron microscopy (SEM) image showing the inhalable human insulin API produced via the method described with respect to Example 1. In the present application, all of the SEM images were obtained using a JEOL CarryScope JCM-5700 SEM instrument. FIG. 3 is a graph illustrating the particle size distribution of the inhalable insulin API (micronized insulin) prepared as described with respect to Example 1. It was concluded from FIGS. 2 and 3 that the particle sizes of the inhalable insulin API (micronized insulin) prepared as described with respect to Example 1 are suitable for pulmonary delivery, e.g., have a particle size <5 μm. For example, as can be seen in FIG. 3, the average particle size D50 of the micronized insulin of Example 1 was less than 2 μm. D50 is the maximum particle diameter below which 50 vol % of the sample, based on the total volume of the sample, has a smaller particle diameter and above which 50 vol % of the sample has a larger particle diameter.

EXAMPLE 2

Batch Process for Preparation of Inhalable Insulin Particles in a 90 Vol % Methanol Solution 1 gram of biosynthetic human insulin API powder (i.e., recombinant insulin from Amphastar France Pharmaceuticals S.A.S.) was dissolved in 110 ml of an acidic solution having a pH of about 1.9 in a mixture of 90 vol % of methanol and 10 vol % water, in a 400 ml beaker with a centrifugal stirrer or stirring bar. The resultant solution was stirred until the insulin solution was completely dissolved or substantially completely clear to form insulin true solution. Then, the stirring was slowed to a slower mode (e.g., a spinning speed of about 50 rpm), and 25 ml of a 0.1 M sodium acetate/Acetic Acid (NaAc/HAc) buffer solution (having a pH of 5.64) was added dropwise to titrate the dissolved insulin solution. The clear dissolved insulin solution turned into a milky and yellowish suspension including micronized insulin particles. After the titration was completed, about 135 ml of ethanol (Neutral ethanol) was added to the suspension, and the stirring was continued for another 30 minutes for stabilizing the particles and higher yield.

The micronized insulin particles were concentrated from the supernatant of the suspension, by ultrafiltration with 500 kD modified polyethersulfone membrane from Spectrum Lab at Rancho Dominguez, Calif. First the mixture was concentrated 5-10 ml, which was washed with 100 ml ethanol three times to remove methanol and salt. The final volume of the suspension is 5 to 10 ml. The concentrated suspension was vacuum dried at room temperature for 2.5 hr. The product weight was used to calculate the recovery rate. The particle size was analyzed using a laser diffraction particle size analyzer (i.e., the JEOL CarryScope JCM-5700 SEM instrument).

The above procedures were repeated four (4) times for batches of micronized insulin.

Table 1 shows reproducibility of the recovery rate for the four (4) batches produced as described with respect to Example 2. As can be seen from Table 1, the recovery rate for Example 2 is over 86%.

TABLE 1

| Process Reproducibility | |
|---|---|
| Batch No. | Recovery Rate % |
| Batch 1 | 86.4 |
| Batch 2 | 86.1 |
| Batch 3 | 86.8 |
| Batch 4 | 86.2 |
| Average | 86.4 |
| Standard Deviation | 0.3 |
| Relative Standard Deviation, % | 0.4% |

Table 2 shows the reproducibility of the particle size distribution of the micronized human insulin particles produced in the batches of Example 2. It was concluded from Table 2 that the particles sizes of the micronized insulin prepared as described with respect to Example 2 are suitable for pulmonary delivery, e.g., having a particle size <5 μm. For example, as can be seen in Table 2, for the micronized insulin of Example 2 the average particle size D50 was 1.54 μm, the average particle size D10 was 0.75 μm, and the average particle size D90 was 3.04 μm, which is suitable for pulmonary delivery. D50 is the maximum particle diameter below which 50 vol % of the sample, based on the total volume of the sample, has a smaller particle diameter than the D50 particle diameter and above which 50 vol % of the sample has a larger particle diameter than the D50 particle diameter. D10 is the particle diameter at which 10 vol % of the particles, based on the total volume of the particles, have a smaller particle diameter than the D10 particle diameter. D90 is the particle diameter at which 90 vol % of the particles, based on the total volume of the particles, have a smaller particle diameter than the D90 particle diameter.

TABLE 2

| Particle Size Measurement for Example 2 | | | | |
|---|---|---|---|---|
| | Particle Size Distribution (μm) | | | |
| Batch No. | D10 | D50 | D90 | Volume Mean Diameter |
| Batch 1 | 0.72 | 1.46 | 2.9 | 1.68 |
| Batch 2 | 0.77 | 1.58 | 3.0 | 1.77 |
| Batch 3 | 0.75 | 1.52 | 2.95 | 1.74 |
| Batch 4 | 0.76 | 1.59 | 3.31 | 1.96 |
| Average | 0.75 | 1.54 | 3.04 | 1.79 |
| Standard Deviation | 0.02 | 0.06 | 0.18 | 0.12 |
| Relative Standard Deviation | 2.9% | 3.9% | 6.1% | 6.8% |

Figure 4:
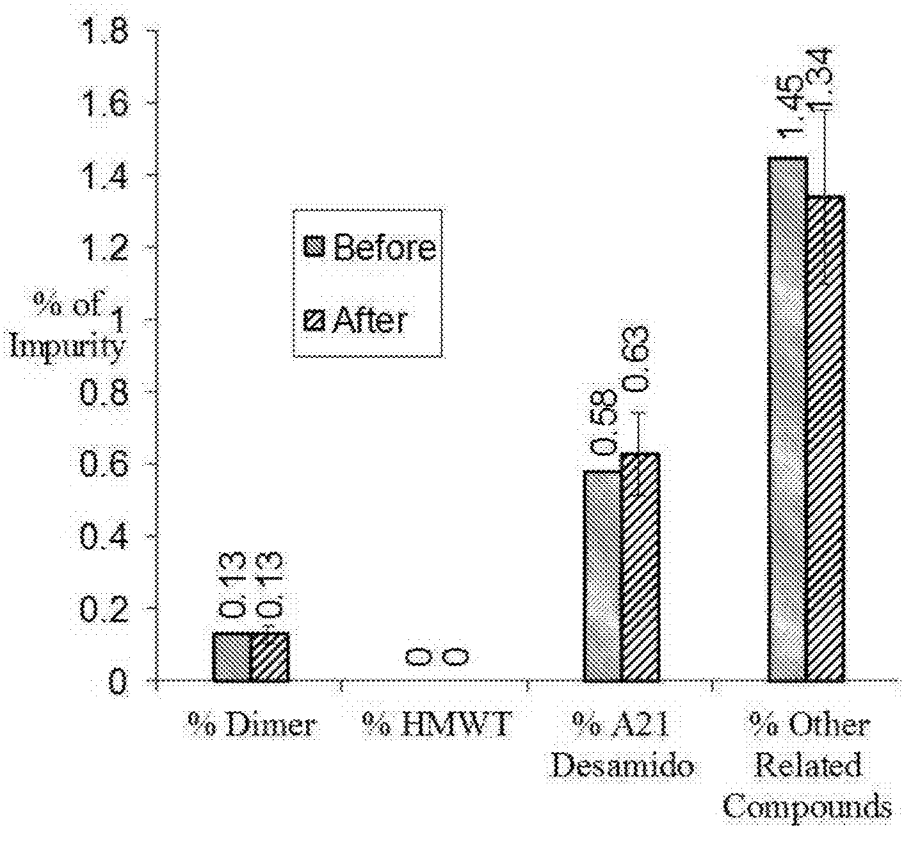
FIG. 4 is a chart showing an impurity profile of human insulin before and after micronizing according to an embodiment of the present disclosure.

The chemical stability of the insulin before and after processing was tested by high performance liquid chromatography (HPLC) according to Chapter <621> of United States Pharmacopeia (USP) and USP methods used for impurity test for the human insulin monograph. FIG. 4 is a chart showing an impurity profile of insulin before and after the micronizing process according to Example 2. As can be seen in FIG. 4, there is not a statistically significant change in the quantity of impurities, such as insulin dimers, high molecular weight proteins, A-21 desamido insulin or related compounds in the insulin during the micronizing process.

Figure 5:
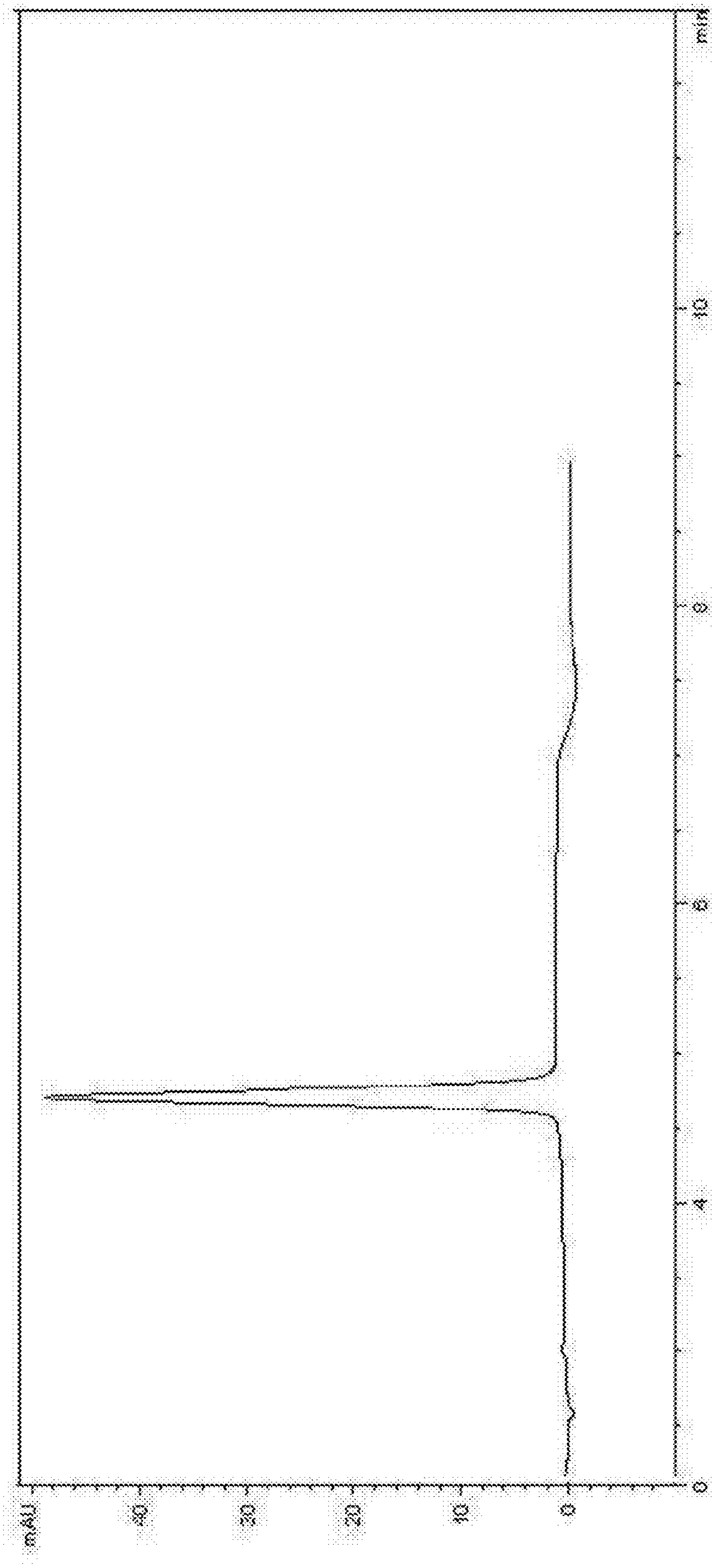
FIG. 5 is a high-performance liquid chromatography (HPLC) chromatograph of dissolved, micronized insulin particles prepared according to an embodiment of the present disclosure.

FIG. 5 is a high-performance liquid chromatography (HPLC) chromatograph of dissolved insulin particles prepared as described in Example 2. The HPLC chromatograph of FIG. 5 shows that the retention time for micronized insulin does not exhibit a statistically significant change with respect to that of the original insulin raw material. The evidence from the analysis of the micronized insulin particles indicates that the chemical integrity of the insulin is maintained or substantially maintained during the micronization process.

Figure 6:
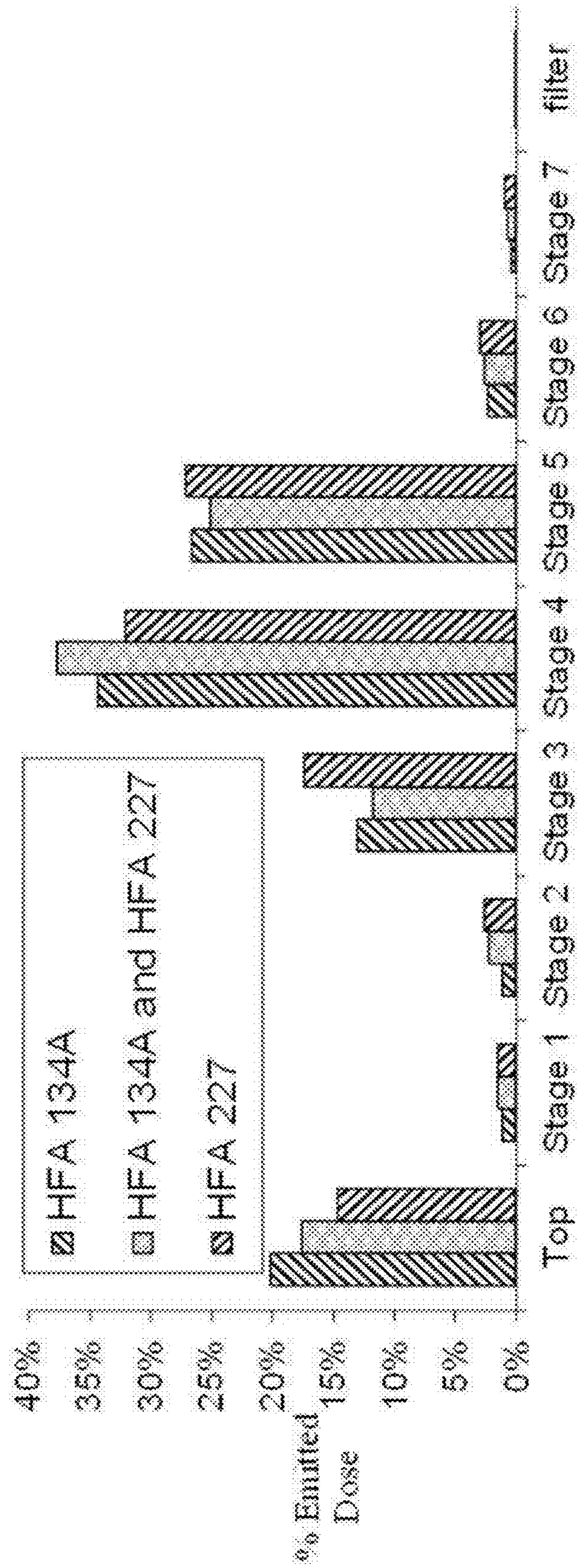
FIGS. 6 and 7 are charts showing data from an Andersen Cascade Impactor study of human insulin particles delivered from a filled canister as prepared according to an embodiment of the present disclosure.

The particle size distribution of the micronized insulin particles was evaluated using a laser diffraction CUVETTE CUV-50ML/US instrument from Sympatec Gmbh. The micronized insulin particles were tested in ethanol media (an ethanol solution). The data indicates that the average of the volume mean diameter for all four (4) batches is 1.79 μm, as shown in Table 2. FIG. 6 is a chart showing Andersen Cascade Impactor studies of the human insulin (API produced as described with respect to Example 2) delivered from three metered dose inhalers utilizing a propellant including 1,1,1,2-tetrafluoroethane (HFA 134A), 1,1,1,2,3,3,3,-heptafluoropropane (HFA 227), or a mixture of HFA 134A and HFA 227, respectively. The metered dose inhalers were prepared as described below with respect to Example 11. It was concluded from the data shown in FIG. 6 that the three different propellants (HFA 134A, HFA 227, and the mixture of HFA 134A and HFA 227) provided comparable results when utilized with the micronized human insulin produced as described with respect to Example 2.

Figure 7:
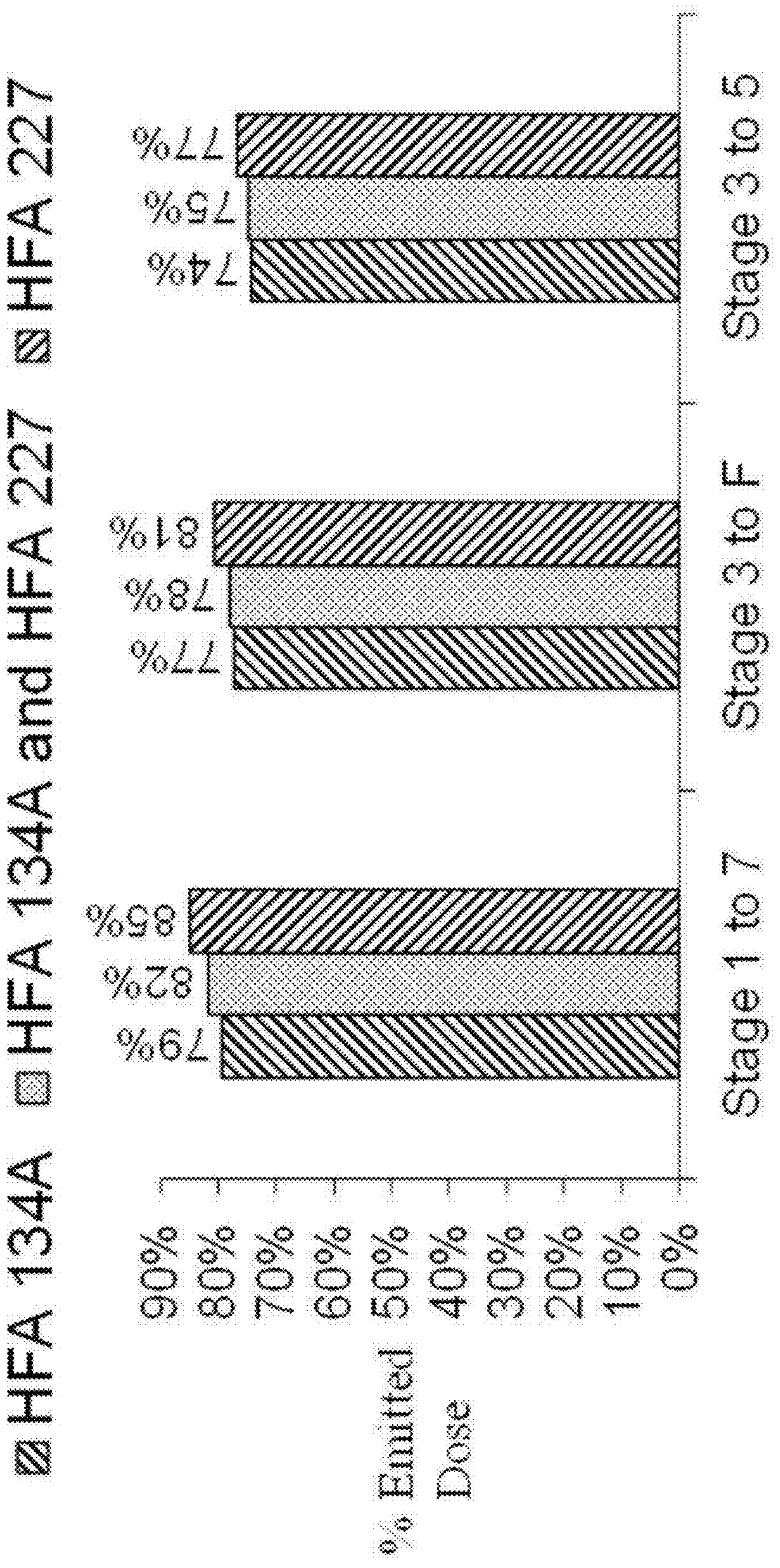

FIG. 7 is a chart further showing the Andersen Cascade Impactor analytical results at three different stage classifications for the human insulin (API produced as described with respect to Example 2) delivered from metered dose inhalers utilizing the three different propellants (HFA 134a, HFA 227, or a mixture of HFA 134A and HFA 227, respectively). The metered dose inhalers were prepared as described below with respect to Example 11. It was concluded from the data shown in FIG. 7 that the three different propellants provided comparable results when utilized with the micronized human insulin produced as described with respect to Example 2, for a pulmonary delivery of insulin.

EXAMPLE 3

Method of Preparation of Inhalable Insulin Particles in a 100 Vol % Water Solution Inhalable human insulin particles were prepared as described with respect to Example 1, except that a roughly 100 vol % purified water solution having a pH of 2.0 (a solution including purified water and an acid in amount sufficient to provide a pH of 2.0) was used to replace the acidic solution including 90 vol % of methanol of Example 1. The particle size distribution of the resultant inhalable human insulin particles was analyzed as described with respect to Example 2. The results of the particle size distribution analysis showed that the inhalable human insulin particles had a volume mean diameter of 2.01 μm. As noted above, the inhalable human insulin particles prepared as described with respect to Example 1 had a particle size D50 of less than 2 μm, and the average of the volume mean diameter of all 4 batches of the inhalable human insulin particles prepared as described with respect to Example 2 (which were also prepared using an acidic solution including 90 vol % methanol) was 1.79 μm. Thus, it can be seen that the composition of the solvent (e.g. methanol vs. water) can change the size of the micronized human insulin that is produced.

EXAMPLE 4

Methods of Preparation of Inhalable Human Insulin Particles in Low Methanol Concentration Solution Inhalable human insulin particles were prepared as described with respect to Example 1, except that an acidic solution including 50 vol % methanol at a pH of about 2.0 (the other 50 vol % including water and HCl) or an acidic solution including 10 vol % methanol (the other 90 vol % including water and HCl), based on the total volume of the acidic solution, was used to replace the acidic solution including 90 vol % methanol utilized to dissolve the human insulin raw material of Example 1.

Table 3 shows particle size distribution data of human insulin particles micronized as described with respect to Examples 1, 3 and 4.

TABLE 3

Particle Size Distributions for examples 1, 3, and 4

| | | Particle Size Distribution (μm) | | | |
|---|---|---|---|---|---|
| ID# | Solvent | D10 | D50 | D90 | Volume Mean Diameter |
| Example 3 | 100 vol % water | 0.65 | 1.63 | 3.92 | 2.01 |
| Example 4 | 10 vol % MeOH | 0.65 | 1.66 | 3.77 | 2.0 |
| Example 4 | 50 vol % MeOH | 0.33 | 0.74 | 1.52 | 0.87 |
| Example 1 | 90 vol % MeOH | 0.72 | 1.51 | 2.94 | 1.71 |

It was therefore concluded that the starting solvent (e.g., methanol solution vs. water) and solvent concentration (e.g., methanol concentration of 10 vol %, 50 vol % or 90 vol %, based on the total volume of the acidic solution) utilized to dissolve human insulin (raw material) may affect the particle size of the micronized human insulin particles.

EXAMPLE 5

Methods of Preparation of Inhalable Human Insulin Particles in a 10 Vol % Ethanol Solution Inhalable human insulin particles were prepared as described with respect to Example 1, except that an acidic solution including 10 vol % ethanol (the other 90 vol % including water and HCl) having a pH of 2 based on the total volume of the acidic solution, was used to replace the acidic solution including 90 vol % methanol utilized to dissolve the insulin of Example 1. The particle size distribution of the resultant inhalable human insulin particles was analyzed as described with respect to Example 2. The results of the particle size distribution analysis showed that the inhalable human insulin particles had a volume mean diameter of 1.36 μm.

EXAMPLE 6

Method for Micronizing Human Insulin to Inhalable Particles Utilizing a 90 Vol % Methanol Solution at a Different pH Inhalable human insulin particles were prepared as described with respect to Example 1, except that instead of utilizing a buffer solution having a pH of 5.64 a series of buffer solutions including NaOH having a pH of 3 to 9 were utilized. The particle size distributions of the resultant inhalable human insulin particles were analyzed as described with respect to Example 2. NaOH was used to adjust the solution pH as well. The results of the particle size distribution analyses and the pH of the corresponding buffer solution after titration are shown in Table 4. It was concluded from the data shown in Table 4 that utilizing a buffer solution having a pH of 3 to 9 is suitable for embodiments of the micronization process. The data obtained shows that over 99 vol % of the particles, based on the total volume of the particles, have a particle size smaller than 5 μm. Thus, the micronized insulin particles may include 99 vol % or more (e.g., 99 to 100 vol %) of particles having a particle size of less than 5 μm, based on the total volume of the micronized insulin particles. In these embodiments, the micronized insulin particles may include up to 99 vol % of particles having a particle size of less than 5 μm, based on the total volume of the micronized insulin particles.

TABLE 4

Insulin Particle Size, Generated at Various pH

| | | Particle Size Distribution (μm) | | | | |
|---|---|---|---|---|---|---|
| # | pH | D10 | D50 | D90 | D99 | Volume Mean Diameter |
| 1 | 3.1 | 0.5 | 1.16 | 2.32 | 3.69 | 1.31 |
| 2 | 5.3 | 0.63 | 1.29 | 2.4 | 3.66 | 1.42 |
| 3 | 6.0 | 0.7 | 1.44 | 2.27 | 4.46 | 1.63 |
| 4 | 6.2 | 0.72 | 1.51 | 2.94 | 4.81 | 1.71 |
| 5 | 7.0 | 0.6 | 1.22 | 2.21 | 3.51 | 1.33 |
| 6 | 7.9 | 0.56 | 1.17 | 2.12 | 3.41 | 1.28 |
| 7 | 8.8 | 0.57 | 1.18 | 2.13 | 3.38 | 1.29 |

EXAMPLE 7

Method of Preparation of Inhalable Human Insulin Particle Utilizing an Isopropyl Alcohol Co-solvent Inhalable human insulin particles were prepared as described with respect to Example 1, except that isopropyl alcohol was used to replace the ethanol of Example 1 that was added to the suspension after the titration was completed or substantially completed. The particle size distribution of the resultant inhalable human insulin particles was analyzed as described with respect to Example 2. The results of the particle size distribution analysis showed that the volume mean diameter of the inhalable human insulin particles was 1.27 μm.

EXAMPLE 8

Method of Preparation of Inhalable Human Insulin Particle Utilizing an Acetone Co-solvent Inhalable human insulin particles were prepared as described with respect to Example 1, except that acetone was used to replace the ethanol of Example 1 that was added to the suspension after the titration was completed or substantially completed. The particle size distribution of the resultant inhalable human insulin particles was analyzed as described with respect to Example 2. The results of the particle size distribution analysis showed that the volume mean diameter of the inhalable human insulin particles was 1.32 μm.

EXAMPLE 9

Method for Micronizing Insulin Glargine Analogue to Inhalable Particles

Figure 8:
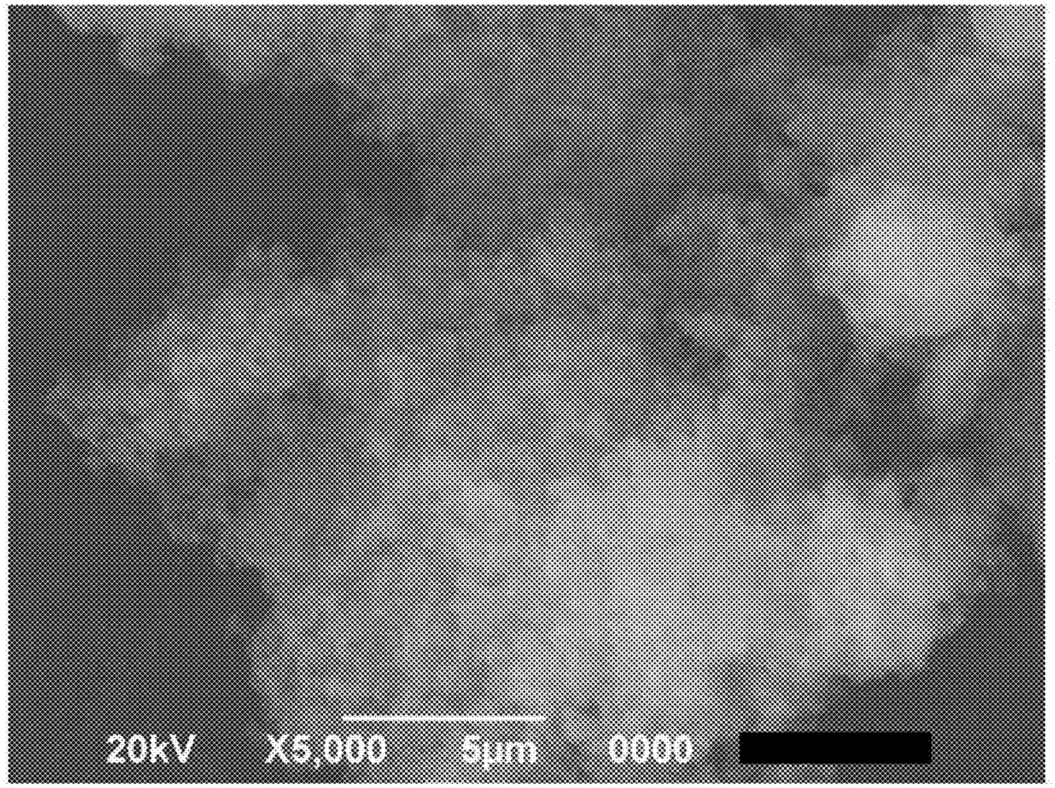
FIG. 8 is a Scanning Electron Microscopy (SEM) image of micronized insulin glargine particles prepared according to an embodiment of the present disclosure.
Figure 9:
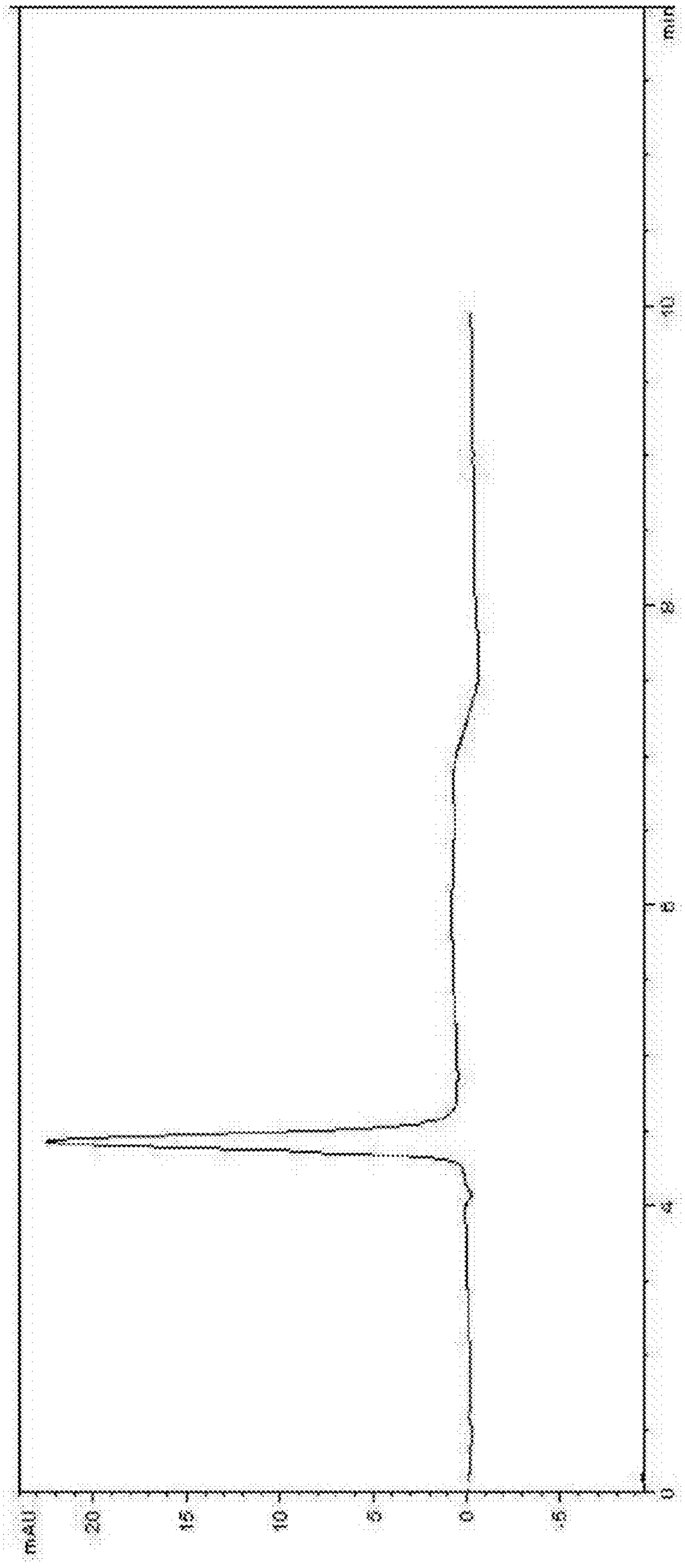
FIG. 9 is an HPLC chromatograph of dissolved, micronized insulin glargine particles prepared according to the embodiment of FIG. 8.
Figure 10:
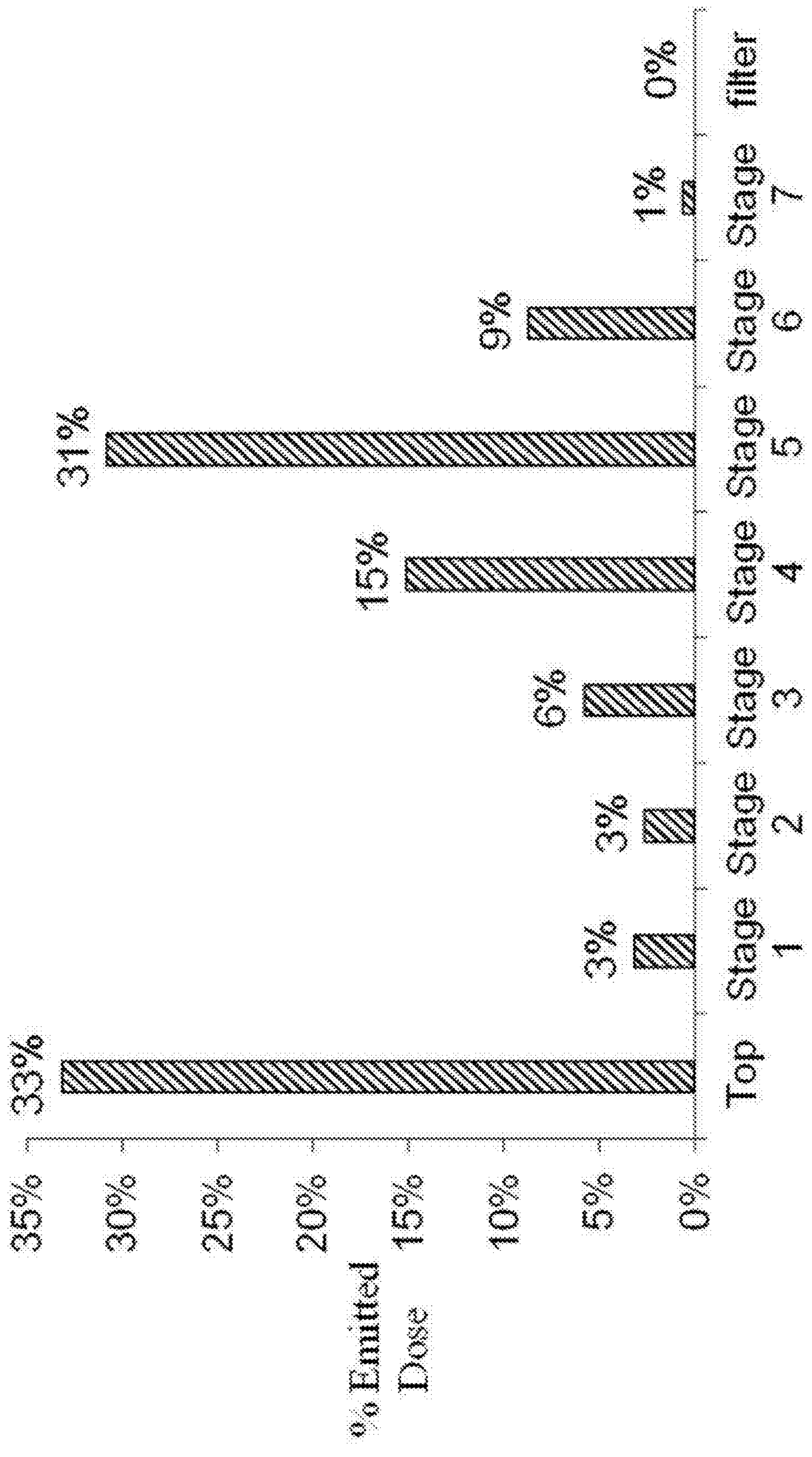
FIGS. 10 and 11 are charts showing the results of an Andersen Cascade Impactor study of insulin glargine particles delivered from a filled canister as prepared according to the embodiment of the present disclosure.
Figure 11:
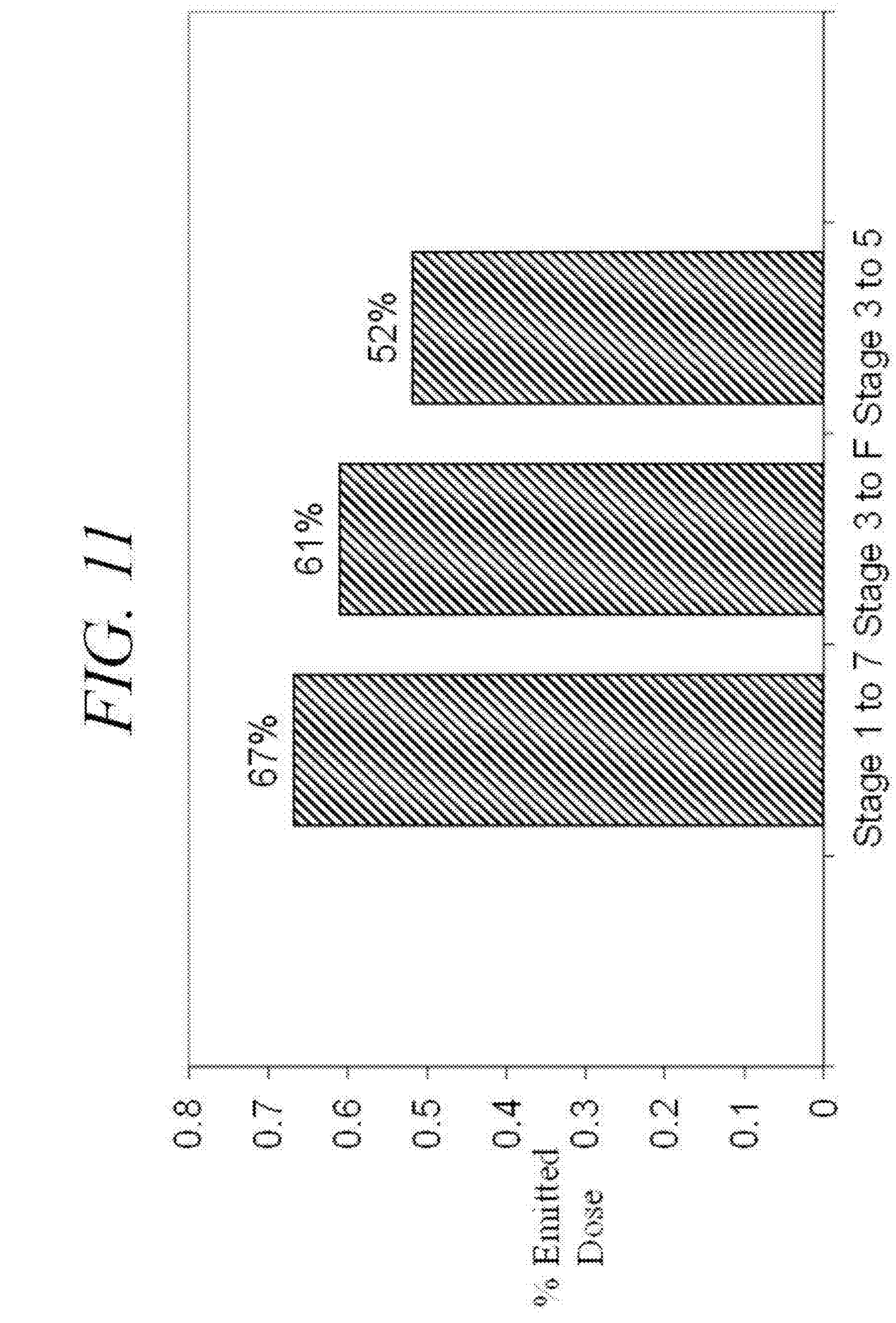

Insulin glargine is a long acting human insulin analogue. The insulin glargine used here was obtained by ultrafiltration of commercially available insulin glargine) (LANTUS®). The insulin glargine was washed and lyophilized before use. 70 mg of the washed and lyophilized insulin glargine was dissolved in 7.7 ml of an acidic solution having a pH of about 2.2, a mixture of 90 vol % methanol and 10 vol % water, based on the total volume of the acidic solution, to form a dissolved insulin solution including an insulin glargine. 1.75 ml of a phosphate buffer solution having a pH of 6.9 was added dropwise to titrate the dissolved insulin glargine solution after the insulin glargine was completely dissolved. 10 ml of ethanol was added to the solution. The foregoing dissolving, titrating, and addition of ethanol were performed under steady (substantially continuous) stirring. The clear dissolved insulin glargine solution becomes a milky suspension including micronized insulin glargine particles (micronized insulin glargine particles). The micronized insulin glargine particles were separated, washed and dried. The particle size distribution of the micronized insulin glargine particles was analyzed using the laser diffraction test described with respect to Example 2. The particle distribution analysis showed that the volume mean diameter of the micronized insulin glargine particles was 2.27 μm. FIG. 8 is a Scanning Electron Microscopy (SEM) image of the micronized insulin glargine particles. FIG. 9 is an HPLC chromatograph of the dissolved micronized insulin glargine particles. Retention time of the HPLC results shown in FIG. 9 indicates that the chemical properties of the insulin glargine did not change (or did not substantially change) during the micronization process. FIGS. 10 and 11 are charts showing the results of an Andersen Cascade Impactor study of the insulin glargine particles delivered from metered dose inhalers utilizing HFA 134A as a propellant. The metered dose inhalers were prepared as described below with respect to Example 11. The study results shown in FIGS. 10 and 11 demonstrated a consistent or substantially consistent pattern for a pulmonary delivery of insulin.

EXAMPLE 10

Method for Micronizing Insulin Aspart Analogue to Inhalable Particles

Figure 12:
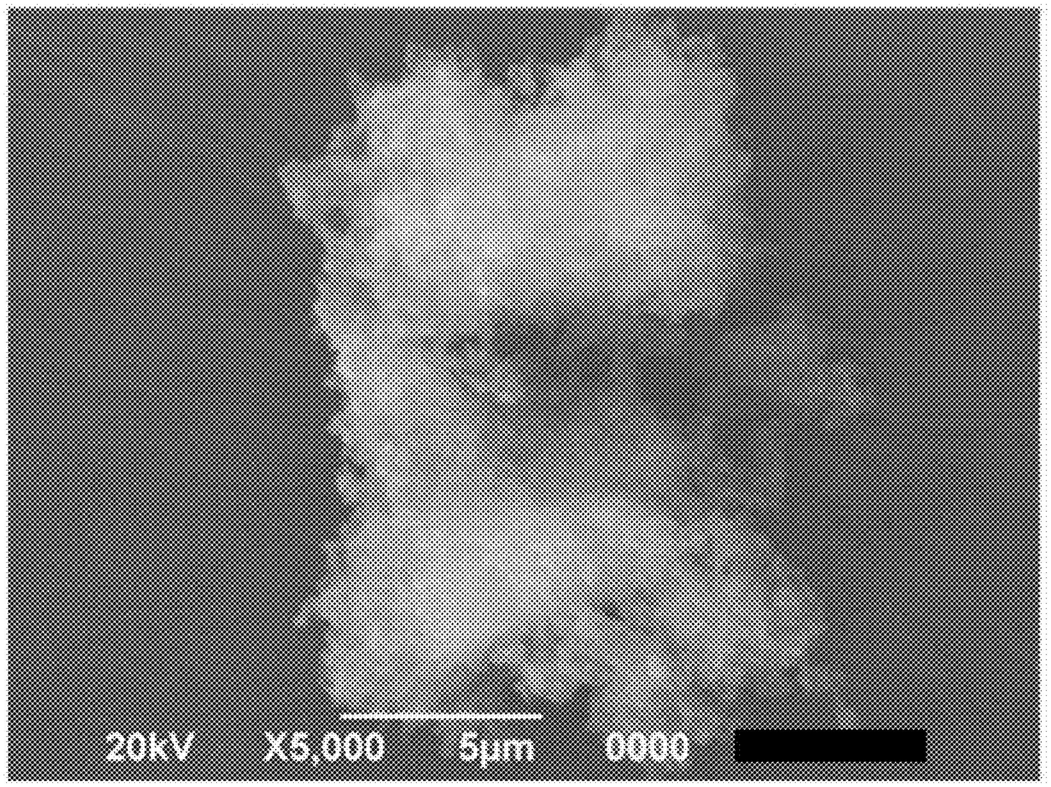
FIG. 12 is a Scanning Electron Microscopy (SEM) image of micronized insulin aspart particles prepared according to an embodiment of the present disclosure.
Figure 13:
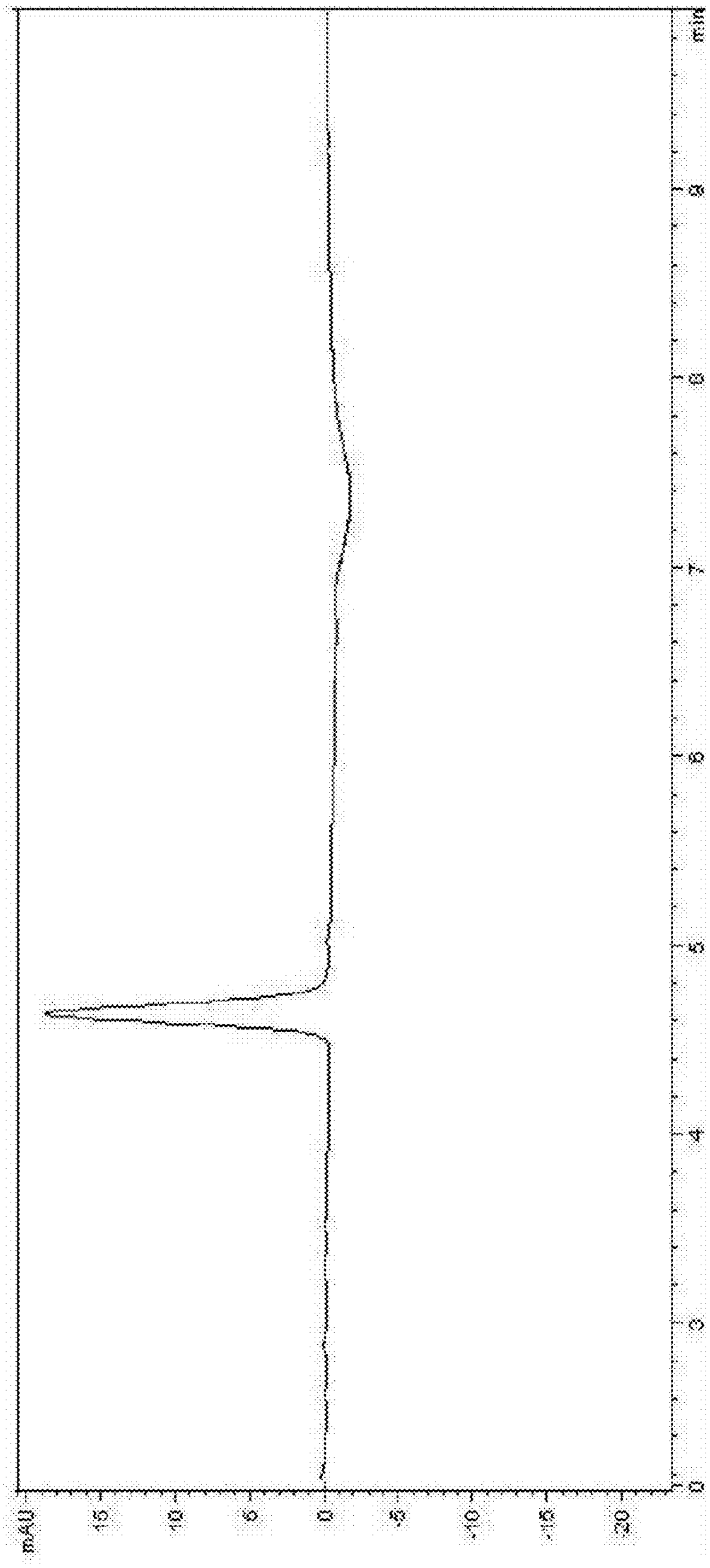
FIG. 13 is an HPLC chromatograph of dissolved micronized insulin aspart particles prepared according to the embodiment of FIG. 12.

Insulin Aspart is a fast-acting insulin analogue. Insulin Aspart used here was obtained by ultrafiltration of NovoLog® (obtained from Novo Nordisk, Bagsværd, Denmark). The ultrafiltered insulin aspart was washed and lyophilized before use. 70 mg of washed and lyophilized insulin aspart was dissolved in 7.7 ml of an acidic water solution having a pH of about 2 and including HCl to form a dissolved insulin solution including insulin aspart. 4.2 ml of an acetate buffer solution having a pH of 5.64 was added dropwise to titrate the dissolved insulin aspart solution after the insulin aspart was completely dissolved. 78 ml of ethanol was added to the solution to obtain a suspension. The foregoing dissolving, titrating, and addition of ethanol were performed under steady (substantially continuous) stirring to stabilize the particles before wash. The clear dissolved insulin aspart solution became a milky suspension including micronized insulin aspart particles (micronized insulin aspart particles). The micronized insulin aspart particles were separated, washed and dried. The particle size distribution of the micronized insulin aspart particles was analyzed using the laser diffraction test described with respect to Example 2. The particle distribution analysis showed that the volume mean diameter of the micronized insulin aspart particles was 2.72 μm. FIG. 12 is a Scanning Electron Microscopy (SEM) image of the micronized insulin aspart particles. FIG. 13 is an HPLC chromatograph of the dissolved micronized insulin aspart particles. Retention time of the HPLC results shown in FIG. 13 indicates that the chemical properties of the insulin aspart did not change (or did not substantially change) during the micronization process.

Figure 14:
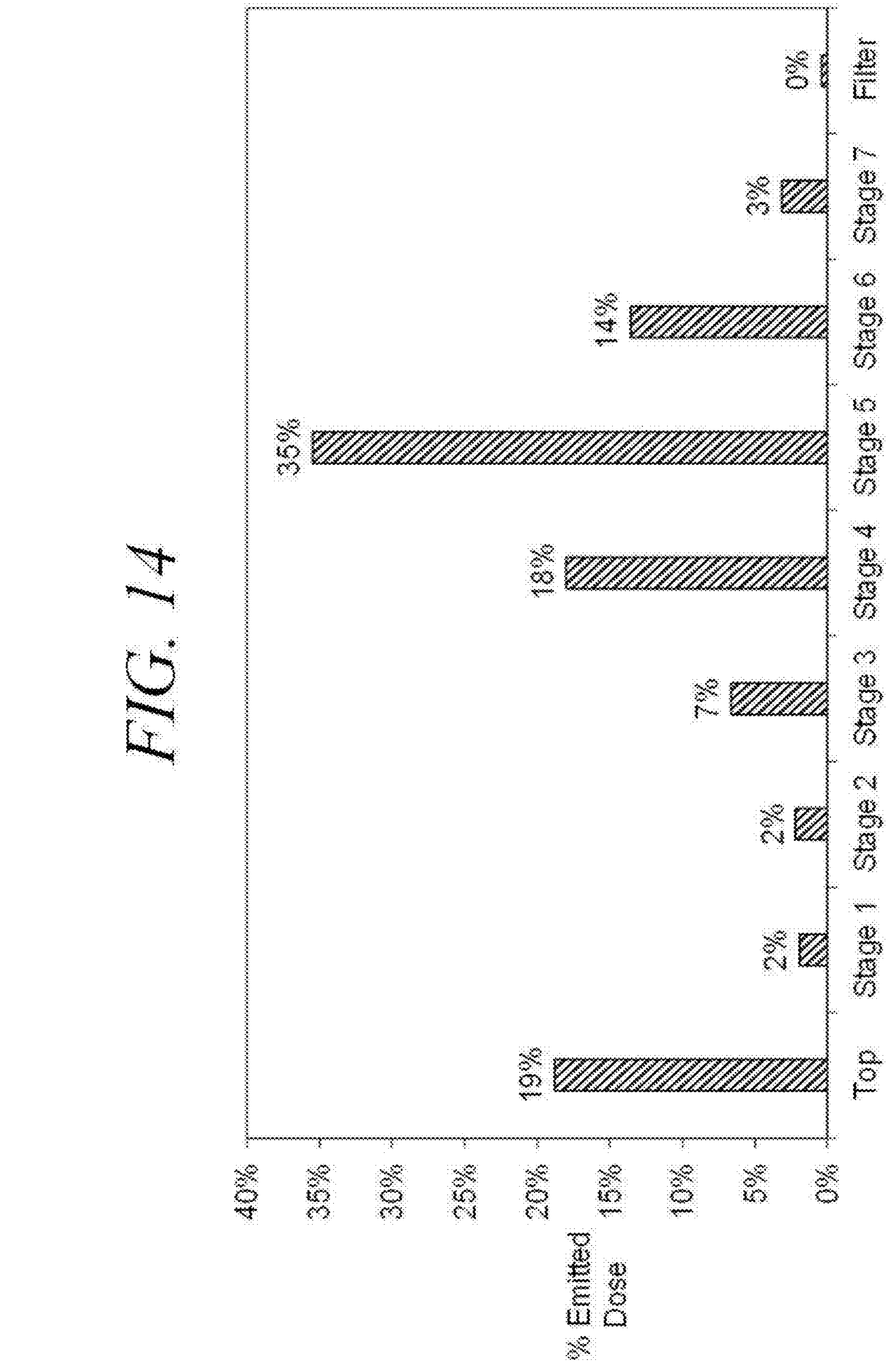
FIGS. 14 and 15 are charts showing results of an Andersen Cascade Impactor study of insulin aspart particles delivered from a filled canister as prepared according to the embodiment of the present disclosure.
Figure 15:
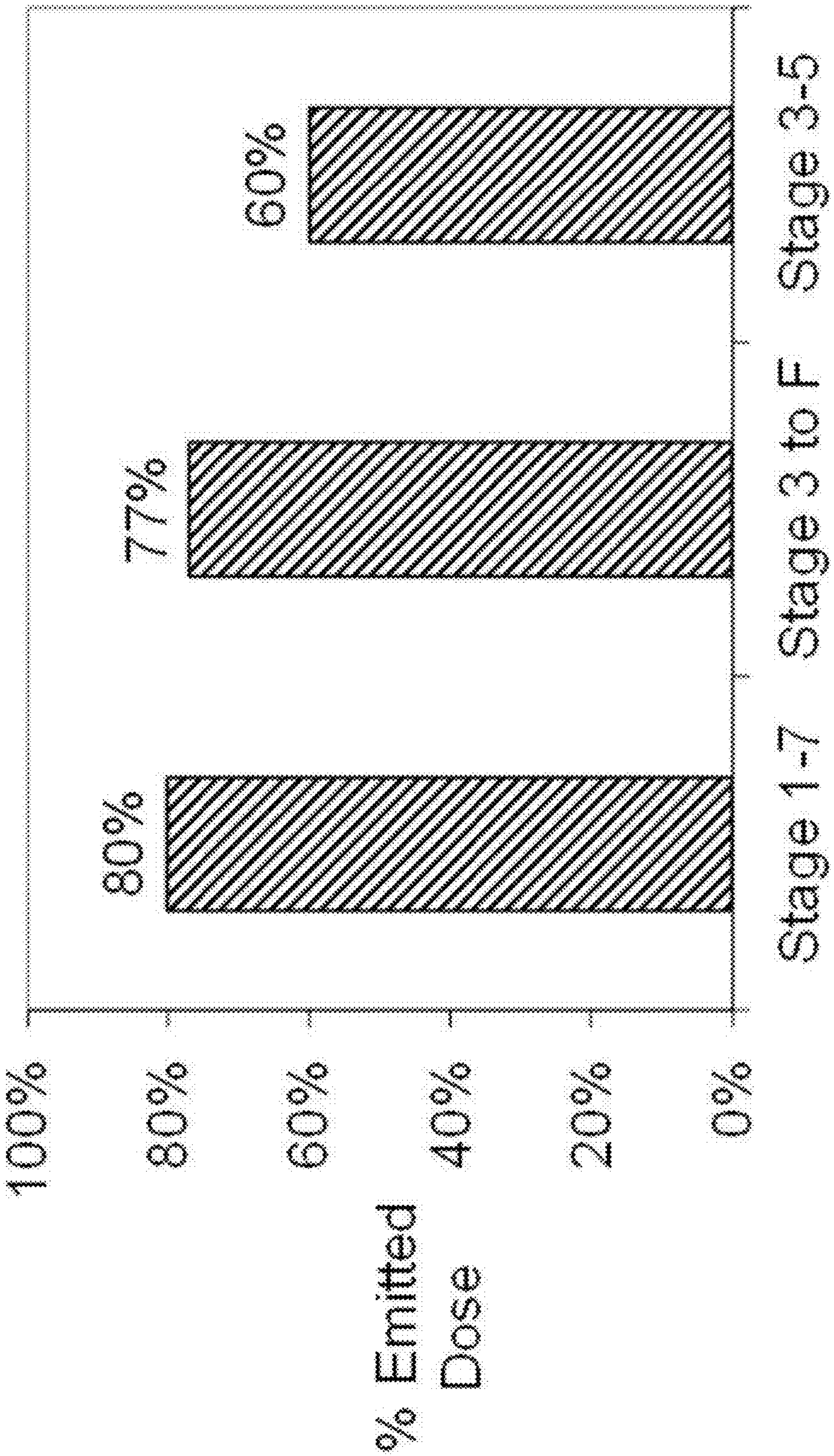

FIGS. 14 and 15 are charts showing the results of an Andersen Cascade Impactor study of the insulin aspart particles delivered from metered dose inhalers utilizing HFA 134A as a propellant. The metered dose inhalers were prepared as described below with respect to Example 11. The study results shown in FIGS. 14 and 15 demonstrated a consistent or substantially consistent pattern for a pulmonary delivery of insulin.

EXAMPLE 11

Preparation of Metered Dose Inhalers for In Vitro Andersen Cascade Impactor Tests Metered dose inhalers (MDIs) were prepared according to the following process. A suitable or appropriate amount of micronized human insulin API (e.g., micronized human insulin particles or micronized human insulin analogue particles) and ethanol were filled into an inhaler canister. The contents of the canister were then mixed by applying ultrasonic energy using a VWR Aquasonic for 5 minutes to achieve a uniform or substantially uniform suspension. Different propellants such as HFA 134A, HFA 227 or a mixture thereof were added, and the canister was sealed utilizing a suitable valve by clamping.

Micronized human insulin (e.g., micronized human insulin particles or micronized insulin analogue particles) was filled into the metered dose inhaler (MDI) as the active ingredient. The concentration of human insulin or insulin analogue in the inhaler was 3 mg/g. The Andersen Cascade Impactor data shown in FIG. 7, FIG. 11, and FIG. 15 correspond well with the particle size distribution results observed utilizing a laser diffraction particle size analyzer. In the Andersen Cascade Impactor data provided herein, emitted dose refers to the percentage of the human insulin or insulin analogue that was deposited on the Andersen Cascade Impactor.

The shape and roughness (or smoothness) of the surface of the human insulin particles micronized by embodiments of the process disclosed herein is quite suitable or favorable (e.g., suitable or favorable for pulmonary delivery). Micronization by jet milling is a common way to grind particles from a millimeter size range to a smaller micrometer size range. The jet milling process involves frequent collisions among the particles as well as collisions with a wall of a milling chamber caused by a high speed gas stream. The micronized particles produced by jet milling are extracted from the milling chamber by a circular motion of a gas stream and centrifugal forces. These mechanical forces may damage the surface and the shape of the micronized particles, for example, as described below with respect to Comparative Example 1, which may not be favorable or suitable for pulmonary delivery.

EXAMPLE 12

High Purity Micronized Inhalable Insulin Particles Suitable for Pharmaceutical Application One (1) gram of biosynthetic human insulin API powder (i.e., recombinant insulin from Amphastar France Pharmaceuticals S.A.S.) was dissolved in 110 ml of an acidic solution having a pH of about 1.9 in a mixture of 90% by volume of methanol and 10% by volume of water in a 400 ml beaker with a centrifugal stirrer or stirring bar. The resultant solution was stirred until the insulin solution was completely dissolved or substantially completely clear to form insulin true solution. Then, the stirring was slowed to a slower mode (e.g., a spinning speed of about 50 rpm), and 25 ml of a 0.1 M NaAc/HAc buffer solution (having a pH of 5.64) was added dropwise to titrate the dissolved insulin solution. The clear dissolved insulin solution turned into a milky and yellowish suspension including micronized insulin particles. After the titration was completed or substantially completed, about 135 ml of ethanol (no pH adjusted) was added to the suspension, and the stirring was continued for another 30 minutes for stabilizing the particle and higher yield.

The micronized insulin particles were separated from the supernatant of the suspension by ultrafiltration and the solid was washed with ethanol twice to remove methanol and salt. The wash and concentration process may be repeated if the solvent impurities are high. The solid was vacuum dried at room temperature. The washing process and concentration of insulin were carried out as described with respect to Example 2 above. The particle size for the resultant micronized insulin is 1.61 μm VMD.

More lots were made with 0.5 g batch for purity and impurity tests using the same process.

The purity and impurity profile of the obtained three (3) batches of insulin particles are tested and listed in Table 5 as follows at dry base (e.g., the results are shown as % by weight relative to the total weight of the insulin particles on a dried basis).

TABLE 5

Test Results Purity and Impurity Profile of Insulin Particles

| | | Insulin-related impurities | | | | Solvent- | Non-Solvent |
|---|---|---|---|---|---|---|---|
| Batch # | Purity | A-21 Desamido | Related Substance | High MW proteins | Total | impurity Methanol | impurity Acetate |
| 1 | 98.7% | 0.39% | 1.1% | 0.32% | 1.8% | <0.001% | 0.07% |
| 2 | 98.8% | 0.36% | 1.1% | 0.30% | 1.7% | <0.001% | 0.04% |

TABLE 5-continued

Test Results Purity and Impurity Profile of Insulin Particles

| | | Insulin-related inpurities | | | | Solvent- | Non-Solvent |
|---|---|---|---|---|---|---|---|
| Batch # | Purity | A-21 Desamido | Related Substance | High MW proteins | Total | impurity Methanol | impurity Acetate |
| 3 | 98.8% | 0.34% | 1.1% | 0.30% | 1.7% | 0.009% | 0.03% |
| Average | 98.8% | 0.36% | 1.1% | 0.31% | 1.8% | 0.009% | 0.05% |

The data in Table 5 shows all three (3) lots:

The purity of the obtained Insulin particles is above 98% (e.g., the purity of insulin in the insulin particles is above 98% by weight, based on the total weight of the insulin particles on a dried basis);

A21 desamido content in the final product was less than 0.40% (e.g., 0.40% by weight based on the total weight of the insulin particles on a dried basis), and micronized insulin's related compounds was around 1.1% (e.g., 1.1% by weight based on the total weight of the insulin particles on a dried basis), less than the 2% by weight of USP criteria;

High molecular weight proteins in human insulin was around 0.3% (e.g., 0.3% by weight based on the total weight of the insulin particles on a dried basis), less than USP criteria of 1%;

The amount of methanol solvent impurity was no more than 0.009% (e.g., 0.009% by weight based on the total weight of the insulin particles on a dried basis);

The amount of acetate non-solvent impurity (acetate salt) was no more than 0.07% (e.g., 0.07% by weight based on the total weight of the insulin particles on a dried basis); and The purity of the resulting insulin particles is more than 98% (e.g., the purity of insulin in the insulin particles is above 98% by weight, based on the total weight of the insulin particles on a dried basis).

EXAMPLE 13

Controlled Zinc Content in Micronized Inhalable Insulin Particles

Seventy (70) mg of biosynthetic human insulin (i.e. recombinant insulin available from Amphastar France Pharmaceuticals S.A.S.) raw material powder was dissolved in 7.7 ml of an acidic solution having a pH of about 1.9 a mixture of 90% by volume of methanol and 10% by volume of water in a 40 ml vial. The vial was placed on top of a stirring plate and the resultant solution was steadily stirred until the solution was completely dissolved or substantially clear to form insulin true solution. Then, the stirring was slowed to a slower mode (e.g., a spinning speed of about 75 rpm), and 1.75 ml of a 0.1 M sodium acetate/acetic acid (NaAc/HAc) buffer solution having a pH of 5.64 was added dropwise to slowly titrate the dissolved insulin solution. The clear dissolved insulin solution turned into a milky and yellowish suspension including micronized insulin particles. About 10 ml of ethanol was added to the suspension after the titration was completed or substantially completed. The stirring was continued for another 30 minutes for stabilizing the particles and to provide higher yield. The micronized insulin particles were separated from a supernatant of the suspension as a solid by centrifuge. The solid was washed with ethanol twice to remove methanol and salt. The solid was vacuum dried at room temperature.

The zinc content in the micronized insulin has no significant changes during the process:

The zinc content before the process in the insulin is 0.39% (e.g., 0.39% by weight based on the total weight of the biosynthetic human insulin), The zinc content after the process in the micronized insulin is 0.42% (e.g., 0.42% by weight based on the total weight of the insulin particles on a dried basis).

Accordingly, in embodiments of the disclosure, the zinc content will be below 1% (e.g., below 1% by weight based on the total weight of the insulin particles on a dried basis) and higher than 0.3% (e.g., higher than 1% by weight based on the total weight of the insulin particles on a dried basis) in the micronized particle if Human Insulin USP was used as starting material.

EXAMPLE 14

Insulin Micronization Process with Higher Recovery Rate

One (1) gram of biosynthetic human insulin API powder (i.e., recombinant insulin from Amphastar France Pharmaceuticals S.A.S.) was dissolved in 110 ml of an acidic solution having a pH of about 1.9 in a mixture of 90% by volume of methanol and 10% by volume of water in a 400 ml beaker with a centrifugal stirrer or stirring bar. The resultant solution was stirred until the insulin solution was completely dissolved or substantially completely clear to form insulin true solution. Then, the stirring was slowed to a slower mode (e.g., a spinning speed of about 50 rpm), and 25 ml of a 0.1 M NaAc/HAc buffer solution (having a pH of 5.64) was added dropwise to titrate the dissolved insulin solution. The clear dissolved insulin solution turned into a milky and yellowish suspension including micronized insulin particles. After the titration was completed about 135 ml of ethanol at 2-8° C. was added to the suspension. The stirring was continued for another 30 minutes under 2-8° C. for stabilizing the particle size and higher yield.

The micronized insulin particles were separated from the supernatant of the suspension as a solid by ultrafiltration and the solid was washed with ethanol twice to remove methanol. The obtained solid of micronized insulin was vacuum dried at room temperature. A mass of 0.92 gram of micronized insulin was obtained. The recovery rate of Insulin with this process is 92% (e.g., the yield of the insulin particles was 92% by weight based on the total weight of the final product).

EXAMPLE 15

Insulin Micronization Process Compatible with MDI Formulation and Compounding One (1) gram of biosynthetic human insulin API powder (i.e., recombinant insulin from Amphastar France Pharmaceuticals S.A.S.) was dissolved in 110 ml of an acidic solution having a pH of about 1.9 in a mixture of 90% by volume of methanol and 10% by volume of water in a 400 ml beaker with a centrifugal stirrer or stirring bar. The resultant solution was stirred until the insulin solution was completely dissolved or substantially completely clear to form insulin true solution. Then, the stirring was slowed to a slower mode (e.g., a spinning speed of about 50 rpm), and 25 ml of a 0.1 M NaAc/HAc buffer solution (having a pH of 5.64) was added dropwise to titrate the dissolved insulin solution. The clear dissolved insulin solution turned into a milky and yellowish suspension including micronized insulin particles. After the titration was completed, about 135 ml of ethanol at 2-8° C. was added to the suspension. The stirring was continued for another 30 minutes at a temperature of 2-8° C. for stabilizing the particle size and resulting in a higher yield before wash.

The micronized insulin particles were concentrated from the supernatant of the suspension by ultrafiltration with 500 kD modified polyethersulfone membrane from Spectrum Lab at Rancho Dominguez, Calif. The suspension of insulin particles was concentrated to 5-10 ml, which was washed with 100 ml ethanol three times to remove impurities, like methanol and salt.

The metered dose inhaler, or MDI product (a pulmonary product) is readily processed and compounded with the obtained insulin particles.

COMPARATIVE EXAMPLE 1

Preparation of Human Insulin Particles Via Jet Milling

Figure 16:
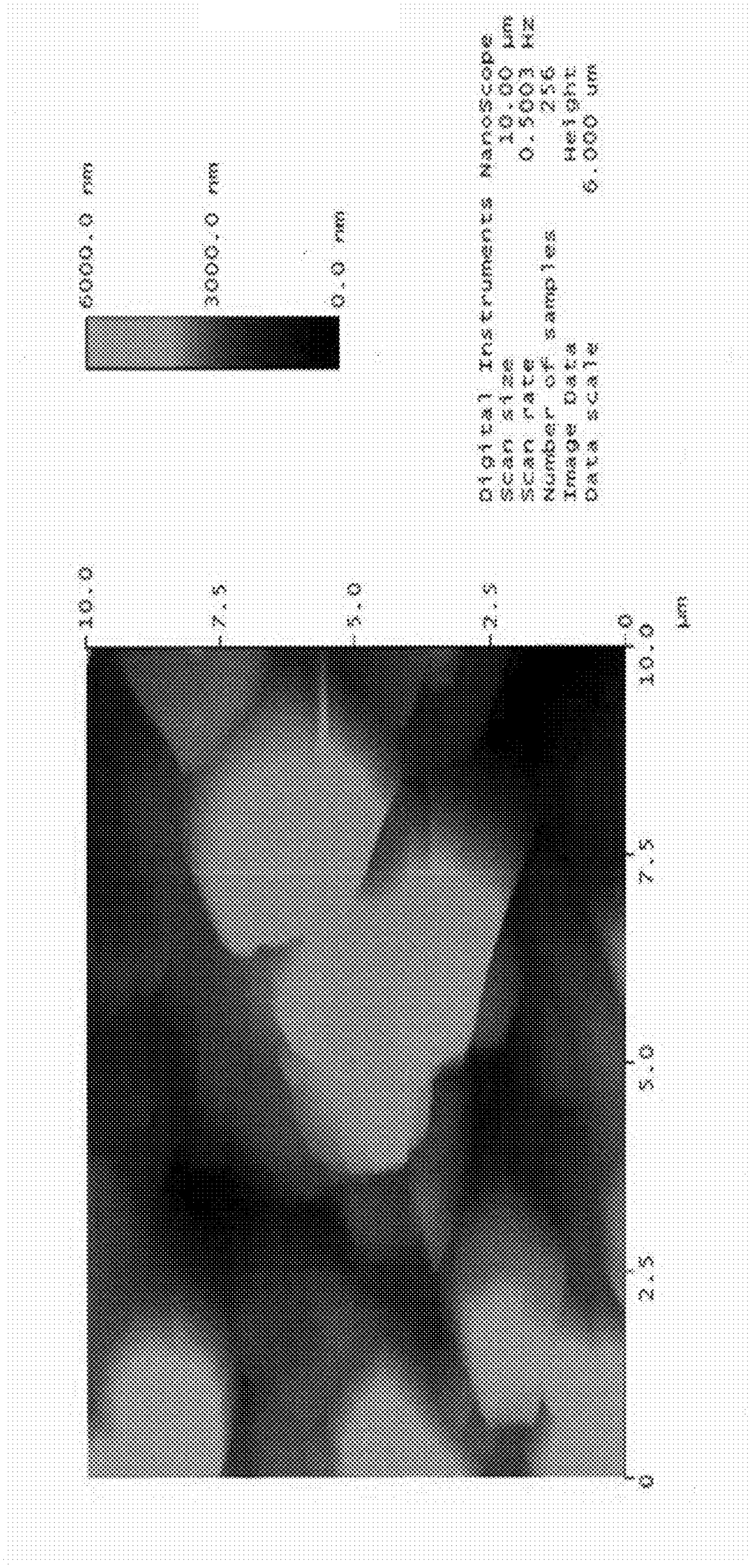
FIG. 16 is an Atom Force Microscopy (AFM) image of human insulin particles prepared according to a jet milling method.

Human Insulin particles were prepared by jet milling utilizing a grinding $N_2$ pressure of 75 PSI and a feeding rate about 1 g/min. FIG. 16 is an atomic force microscopy (AFM) image of human insulin particles that were micronized using the jet milling method. As can be seen in the image of FIG. 16, the human insulin particles prepared by jet milling have a rough and irregular (or uneven) appearance.

Figure 17:
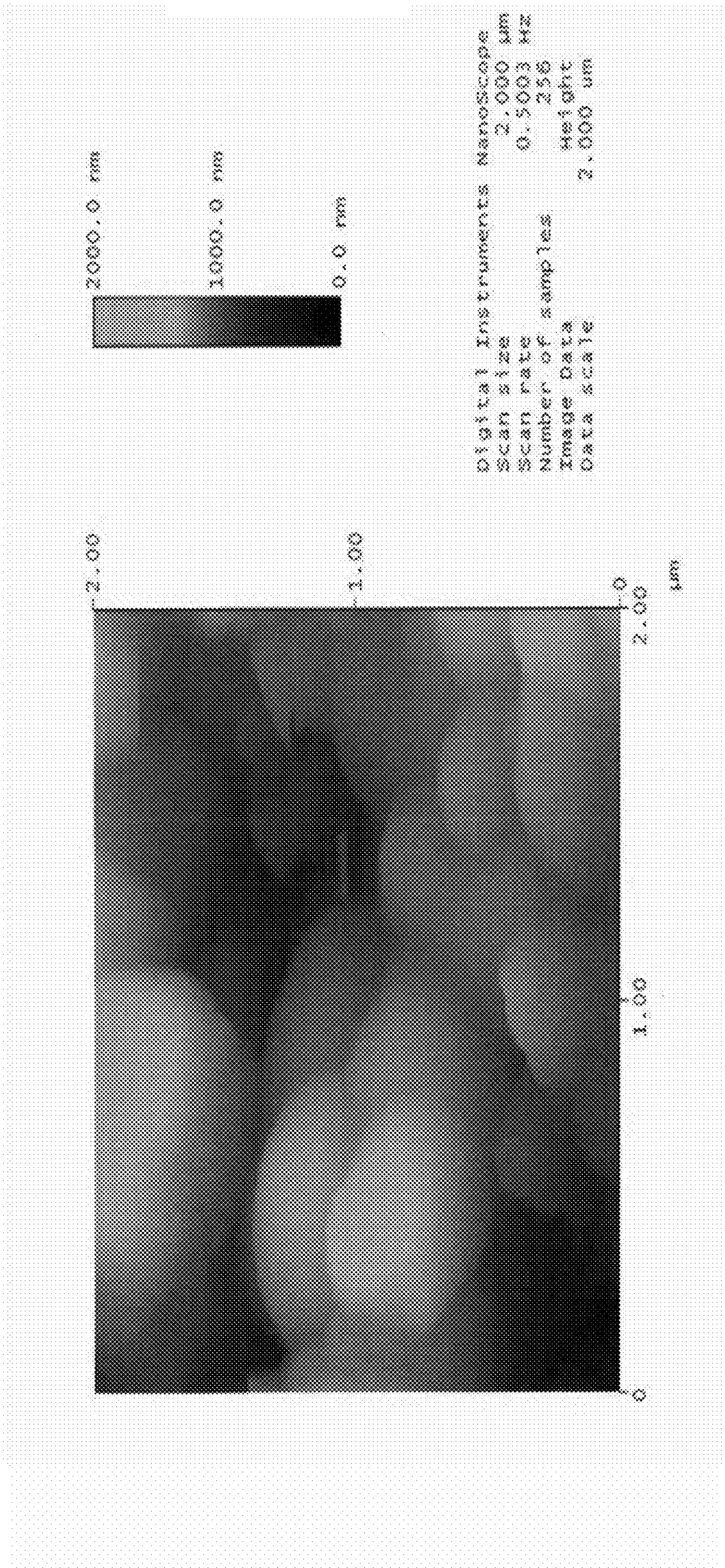
FIG. 17 is an Atom Force Microscopy (AFM) image of micronized insulin particles that were prepared as described with respect to Example 2.

FIG. 17 is an AFM image of inhalable human insulin particles micronized as described with respect to Example 2. Since embodiments of the process disclosed herein are carried out at room temperature and involve no mechanical forces and/or heat (or substantially no mechanical forces and/or heat), the micronized human insulin particles have a shape and surface that are more suitable or more preferred for human pulmonary delivery.

According to an embodiment, a high-purity inhalable insulin material for a pulmonary pharmaceutical product, includes: insulin particles having a particle size at the micrometer level, and having the following characteristics: (i) the purity of the insulin particles being not less than 96% by weight on the dried basis (e.g., insulin being present in the insulin particles in an amount of not less than 96% by weight based on the total weight of the insulin particles on a dried basis); (ii) optionally, the amount of zinc in the insulin particles being not more than 1%, and not less than 0.3% by weight, on a dried basis (e.g., not more than 1% by weight and not less than 0.3% by weight based on the total weight of the insulin particles on a dried basis); (iii) the total amount of insulin-related impurities in the insulin particles being not more than 2% by weight (e.g., not more than 2% by weight based on the total weight of the insulin particles on a dried basis); (iv) the total amount of solvent-related impurities in the insulin particles, which solvent-related impurities do not include a co-solvent formulation component in the pulmonary product, being not more than 0.03% by weight (e.g., not more than 0.03% by weight based on the total weight of the insulin particles on a dried basis); and the total amount of nonsolvent-related impurities in the insulin particles being not more than 0.3% by weight (e.g., not more than 0.3% by weight based on the total weight of the insulin particles on a dried basis). The insulin particles may further include any or all of the following characteristics.

The micronized insulin particles may include an insulin selected from human insulin, an animal insulin, an insulin analogue, and any mixture thereof.

The insulin analogue may be selected from insulin aspart, insulin glargine, and any mixture thereof.

The insulin particles may be substantially spherical (e.g., generally spherical) in shape and have a particle size of less than 5 μm.

99% by volume of the insulin particles may include particles having a particle size of less than 5 μm, based on the total volume of the micronized insulin particles.

The insulin particles may include substantially spherical (e.g., generally spherical) particles having a volume mean particle diameter (e.g., D50) of about 1 μm to 2 μm.

According to an embodiment, a high-efficiency method of preparing a high-purity inhalable insulin having a particle size at the micrometer level suitable for a pharmaceutical pulmonary product, the method including: (1) dissolving an insulin raw material in an acidic solution to form a dissolved insulin solution; (2) titrating the dissolved insulin solution with a buffer solution to form a suspension including insulin particles (e.g., micronized insulin particles) having a particle size at the micrometer level; (3) stabilizing the insulin particles (e.g., the micronized insulin particles) with a solvent; (4) concentrating the suspension including the insulin particles (e.g., the micronized insulin particles); and washing the suspension with a solvent and further concentrating the suspension, where the resultant washed and concentrated suspension including the micronized insulin particles is ready and suitable for further processing to form a pulmonary product, and where the method results in (e.g., provides) the insulin particles having the particle size at the micrometer level, in which 99% (e.g., 99% by volume) of the insulin particles (e.g., the micronized insulin particles) have a particle size less than 5 μm and the volume mean particle diameter (e.g., D50) of the insulin particles (e.g., the micronized insulin particles) is about 1 μm to 2 μm, and in which the purity of the insulin particles is not less than 96% on the dried basis (e.g., an amount of insulin in the insulin particles is not less than 96% by weight based on the total weight of the insulin particles on a dried basis); optionally, the amount of zinc in the insulin particles is not more than 1% (e.g., not more than 1% by weight based on the total weight insulin particles on a dried basis), and not less than 0.3% by weight on the dried basis (e.g., based on the total weight of the insulin particles on a dried basis); the total amount of all insulin-related impurities in the insulin particles is not more than 2% (e.g., not more than 2% by weight based on the total weight of the insulin particles on a dried basis); the total amount of solvent-related impurities in the insulin particles, which solvent-related impurities do not include a co-solvent formulation component in the pulmonary product, is not more than 0.03% (e.g., not more than 0.03% by weight based on the total weight of the insulin particles on a dried basis); and the total amount of nonsolvent-related impurities in the insulin particles is not more than 0.3% (e.g., not more than 0.3% by weight based on the total weight of the insulin particles on a dried basis). The method may further include any or all of the following.

The insulin raw material may include a crystalline insulin selected from crystalline human insulin, crystalline animal insulin, crystalline insulin analogue (e.g., a crystalline human insulin analogue), and any mixture thereof.

The crystalline insulin analogue may be selected from the group consisting of crystalline insulin aspart, crystalline insulin glargine, and any mixture thereof.

The acidic solution may include water and methanol.

The acidic solution may include methanol in an amount of 10% to 90% by volume, based on the total volume of the acidic solution.

The acidic solution may have a pH in the range of 1 to 3.

The acidic solution may have a pH in the range of 1.5 to 2.5.

The acidic solution may be prepared at room temperature.

The titrating of the acidic solution is performed using a buffer solution including sodium acetate and acetic acid.

The titrating may be performed at a pH in the range of 3 to 9.

The titrating may be performed at a pH in the range of 4.5 to 7.5.

The titrating may be performed at room temperature.

The stabilizing may include adding a stabilizing agent including ethanol to the suspension.

The volume of the stabilizing agent including ethanol may be 0.5 to 2 times larger than the volume of the insulin solution (e.g., the dissolved insulin solution).

The stabilizing agent including ethanol may have a neutral pH.

The stabilizing agent including ethanol may be at temperature in the range of 0 to 25° C.

In some embodiments, the adding of the stabilizing agent increases the yield of the insulin particles.

The washing of the suspension including the insulin particles may include washing the suspension with ethanol.

The ethanol may be at a temperature of 0 to 25° C.

The suspension may be a concentrated suspension.

In some embodiments, the resultant concentrated suspension including the insulin particles and the ethanol, and dried insulin particles prepared from the resultant concentrated suspension, are ready for the further processing to form the pulmonary product.

The washing and concentrating may be repeated multiple times (e.g., a plurality of times).

The yield of the inhalable insulin particles may be 75% or greater (e.g., the yield of the inhalable insulin particles may be 75% by weight or greater, based on the total amount of the final product, for example, on a dried basis).

The yield of the inhalable insulin particles may be 85% by weight or greater (e.g., the yield of the inhalable insulin particles may be 85% by weight or greater, based on the total weight of the final product).

While the present invention has been described in connection with certain embodiments, it is to be understood that the invention is not limited to the disclosed embodiments, but, on the contrary, is intended to cover various modifications and equivalent arrangements included within the spirit and scope of the appended claims, and equivalents thereof. Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

What is claimed is:

1. A method of preparing a high-purity inhalable insulin having a particle size at the micrometer level suitable for a pharmaceutical pulmonary product to be delivered by metered dose inhaler, the method comprising:

(1) dissolving insulin in an acidic solution to form a dissolved insulin solution;

(2) titrating the dissolved insulin solution with a buffer solution to form a suspension comprising micronized insulin particles having a particle size at the micrometer level;

(3) stabilizing the micronized insulin particles with a stabilizing agent comprising an alcohol, a ketone, or a mixture thereof, the alcohol is selected from the group consisting of methanol, ethanol, isopropanol, or a mixture thereof, and the ketone is acetone;

(4) concentrating the suspension comprising the micronized insulin particles;

(5) washing the suspension with a solvent and further concentrating the suspension; and (6) separating the micronized insulin particles from a supernatant of the suspension;

(7) wherein the resultant micronized insulin particles are ready and suitable for further processing to form a pulmonary product, and (8) wherein the method provides the insulin particles having the particle size at the micrometer level, in which 99% by volume of insulin particles have a particle size less than 5 μm and the volume mean particle diameter of the insulin particles is about 1 μm to 2 μm, and in which the purity of the insulin particles is not less than 96% by weight on the dried basis; the amount of zinc in the insulin particles is not more than 1% by weight, and not less than 0.3% by weight on the dried basis; the total amount of all insulin-related impurities in the insulin particles is not more than 2% by weight on the dried basis; the total amount of solvent-related impurities in the insulin particles, which solvent-related impurities do not include a co-solvent formulation component in the pulmonary product, is not more than 0.03% by weight on the dried basis; and the total amount of nonsolvent-related impurities in the insulin particles is not more than 0.3% by weight on the dried basis.

2. The method of claim 1, wherein the insulin comprises a crystalline insulin selected from the group consisting of crystalline human insulin, crystalline animal insulin, crystalline insulin analogue, and any mixture thereof.

3. The method of claim 2, wherein the crystalline insulin analogue is selected from the group consisting of crystalline insulin aspart, crystalline insulin glargine, and any mixture thereof.

4. The method of claim 1, wherein the acidic solution comprises water and methanol.

5. The method of claim 4, wherein the acidic solution comprises methanol in an amount of 10% to 90% by volume, based on the total volume of the acidic solution.

6. The method of claim 4, wherein the acidic solution has a pH in the range of 1 to 3.

7. The method of claim 4, wherein the acidic solution has a pH in the range of 1.5 to 2.5.

8. The method of claim 4, wherein the acidic solution is prepared at room temperature.

9. The method of claim 1, wherein the titrating of the acidic solution is performed using a buffer solution comprising sodium acetate and acetic acid.

10. The method of claim 9, wherein the titrating is performed at a pH in the range of 3 to 9.

11. The method of claim 9, wherein the titrating is performed at a pH in the range of 4.5 to 7.5.

12. The method of claim 9, wherein the titrating is performed at room temperature.

13. The method of claim 1, wherein the stabilizing agent comprises ethanol.

14. The method of claim 13, wherein the volume of the stabilizing agent comprising ethanol is 0.5 to 2 times of the volume of the dissolved insulin solution.

15. The method of claim 13, wherein the stabilizing agent comprising ethanol has a neutral pH.

16. The method of claim 13, wherein the stabilizing agent comprising ethanol is at temperature in the range of 0 to 25° C.

17. The method of claim 1, wherein the washing of the suspension comprising the insulin particles comprises washing the suspension with ethanol.

18. The method of claim 17, wherein the ethanol is at a temperature of 0 to 25° C.

19. The method of claim 17, wherein the suspension is a concentrated suspension.

20. The method of claim 19, wherein the resultant concentrated suspension comprising the insulin particles and the ethanol, and dried insulin particles prepared from the resultant concentrated suspension, are ready for the further processing to form the pulmonary product.

21. The method of claim 1, wherein the washing and concentrating are repeated a plurality of times.

22. The method of claim 1, wherein the yield of the inhalable insulin particles is 75% by weight or greater, based on the total amount of the final product.

23. The method of claim 1, wherein the yield of the inhalable insulin particles is 85% by weight or greater, based on the total weight of the final product.

24. A method of preparing a high-purity inhalable insulin having a particle size at the micrometer level suitable for a pharmaceutical pulmonary product, the method comprising:

(1) dissolving insulin in an acidic solution to form a dissolved insulin solution;

(2) titrating the dissolved insulin solution with a buffer solution to form a suspension comprising micronized insulin particles having a particle size at the micrometer level;

(3) stabilizing the micronized insulin particles with a solvent comprising an alcohol, the alcohol is selected from the group consisting of methanol, ethanol, or a mixture thereof;

(4) concentrating the suspension comprising the micronized insulin particles;

(5) washing the suspension with a solvent and further concentrating the suspension, and (6) separating the micronized insulin particles from a supernatant of the suspension, (7) wherein the resultant micronized insulin particles are ready and suitable for further processing to form a pulmonary product, and (8) wherein the method provides the insulin particles having the particle size at the micrometer level, in which 99% by volume of insulin particles have a particle size less than 5 μm and the volume mean particle diameter of the insulin particles is about 1 μm to 2 μm, and in which the purity of the insulin particles is not less than 96% by weight; the total amount of all insulin-related impurities in the insulin particles is not more than 2% by weight; the total amount of solvent-related impurities in the insulin particles, which solvent-related impurities do not include a co-solvent formulation component in the pulmonary product, is not more than 0.03% by weight; and the total amount of nonsolvent-related impurities in the insulin particles is not more than 0.3% by weight, each of the foregoing % by weight being based on the total weight of the insulin particles.

* * * * *